(12) United States Patent
Moretta et al.

(10) Patent No.: US 7,138,243 B2
(45) Date of Patent: Nov. 21, 2006

(54) NTB-A, A SURFACE MOLECULE INVOLVED IN NATURAL KILLER CELLS ACTIVITY

(75) Inventors: Alessandro Moretta, Genoa (IT); Cristina Bottino, Genoa (IT); Roberto Biassoni, Genoa (IT)

(73) Assignees: Innate Pharma, S.A., Marseilles (FR); University of Genova, Genoa (IT)

( * ) Notice: Subject to any disclaimer, the term of this patent is extended or adjusted under 35 U.S.C. 154(b) by 19 days.

(21) Appl. No.: 10/484,139

(22) PCT Filed: Jul. 17, 2002

(86) PCT No.: PCT/EP02/07945

§ 371 (c)(1), (2), (4) Date: Jan. 16, 2004

(87) PCT Pub. No.: WO03/008449

PCT Pub. Date: Jan. 30, 2003

(65) Prior Publication Data

US 2005/0159332 A1 Jul. 21, 2005

(30) Foreign Application Priority Data

Jul. 19, 2001 (EP) ................................. 01401946

(51) Int. Cl.
*G01N 33/53* (2006.01)
(52) U.S. Cl. .................. 435/7.1; 435/4; 424/144.1
(58) Field of Classification Search ............ 435/4–7.2, 435/69.1, 320.1, 325, 183; 436/518; 530/350, 530/388.1, 23.2; 424/144.1
See application file for complete search history.

(56) References Cited

U.S. PATENT DOCUMENTS

| 2003/0092017 | A1* | 5/2003 | Finger ............................ 435/6 |
| 2003/0180888 | A1 | 9/2003 | Fraser | |
| 2004/0005317 | A1 | 1/2004 | Dedera et al. | |
| 2004/0009491 | A1* | 1/2004 | Birse et al. .................... 435/6 |
| 2005/0027114 | A1 | 2/2005 | Kuo et al. | |

FOREIGN PATENT DOCUMENTS

WO    WO 01 55336 A    8/2001

OTHER PUBLICATIONS

EMBL online accession No. AW851581, created May 24, 2000, accessible at http://www.ebi.ac.uk/cgi-bin/emblfetch?style=html&id=aw851581.*
Palmieri et al. "NK cell receptors and signalling", Research in Immunology, 1997, vol. 148, pp. 184-190.*
Birse et al. "Nucleic acids, proteins, and antibodies", WO200190304, 2001, pp. 1-2.*
Bottino, C. et al. "NTB-A, a novel SH2D1A-associated surface molecule contributing to the inability of natural killer cells to kill Epstein-Barr virus-infected B cells in X-linked lymphoproliferative disease." *J. Exper. Med.* (2001) 194(3):235,246.
Moretta, L. et al. "Human NK-cell receptors." *Immunol. Today* (2000) 21(9):420-422.
Moretta, A. et al. "Natural cytotoxicity receptors that trigger human NK-cell-mediated cytolysis." *Immunol. Today* (2000) 21(5):228-234.
Bauer, S. et al. "Activation of NK cells and T cells by NKG2D, a receptor for stress-inducible MICA" Science 285 :727-729, 1999.
Biassoni, R. et al. "CD-3-negative lymphokine-activated cytotoxic cells express the CD3ε gene" J. Immunol. 140:1685-1689, 1988.
Biassoni, R. et al. "The murine homologue of the human NKp46, a triggering receptor involved in the induction of natural cytotoxicity" Eur. J. Immunol. 29:1014-1020, 1999.
Boles, K.S. et al. "Molecular characterization of a novel human natural killer cell receptor homologous to mouse 2B4" Tissue Antigens 54:27-34, 1999.
Bosselut, R. et al. "Association of the adaptor molecule LAT with CD4 and CD8 coreceptors identifies a new coreceptor function in T cell receptor signal transduction" J. Exp. Med. 190(10:1517-1525, 1999.
Bottino, C. et al. "Analysis of the molecular mechanism involved in 2B4-mediated NK cell activation: Evidence that human 2B4 is physically and functionally associated with the linker for activation of T cells" Eur. J. Immunol. 30:3718-3722, 2000.
Cantoni, C. et al. "NKp44, a trigerring receptor involved in tumor cell lysis by activated human natural killer cells, is a novel member of the immunoglobulin superfamily" J. Exp. Med. 189(5):787-795.
Cantoni, C. et al. "Molecular and functional characterization of IRp60, a member of the immunoglobulin superfamily that functions as an inhibitory receptor in human NK cells" Eur. J. Immunol. 29:3148-3159, 1999.
Chang, C. et al. "Cutting edge: Kap10, a novel transmembrane adapter protein genetically linked to DAP12 but with unique signaling properties" J. Immunol. 163:4651-4654, 1999.
Coffey, A. et al. "Host-response to EBV infection in X-linked lymphoproliferative disease results from mutations in an SH2-domain encoding gene" Nature Genetics 20:129-135, 1998.
Davis, S.J. and P.A. van der Merwe. "The structure and ligand interactions of CD2: Implications for T-cell function" Immunology Today 17(4):177-187, 1996.
De La Fuente, M.A. et al. "CD84 leukocyte antigen is a new member of the 1g superfamily" Blood 90(6) :2398-2405, 1997.
Garni-Wagner, B.A. et al. "A novel function-associated molecule related to non-MHC-restricted cytotoxocity mediated by activated natural killer cells and T cells" J. Immunol. 151:60-70, 1993.

(Continued)

*Primary Examiner*—Long V. Le
*Assistant Examiner*—Unsu Jung
(74) *Attorney, Agent, or Firm*—Saliwanchik, Lloyd & Saliwanchik

(57) ABSTRACT

The present invention relates to a novel protein, termed NTB-A, nucleic acid molecules encoding the same and uses thereof. The invention also relates to methods of regulating Natural Killer cells activity by regulating the activity of NTBA-A in vitro, ex vivo or in vivo. The invention also comprises methods of screening active compounds using NTB-A or fragments thereof, or nucleic acid encoding the same, or recombinant host cells expressing said polypeptide.

3 Claims, 7 Drawing Sheets

OTHER PUBLICATIONS

Figure 1:
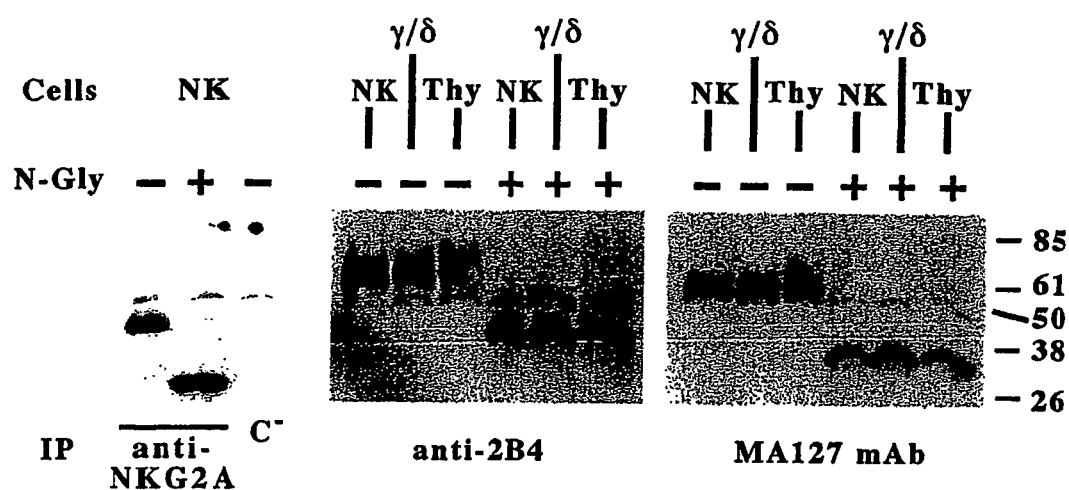

Garrido, F. et al. "Implications for immunosurveillance of altered HLA class I phenotypes in human tumours" Immunol. Today 18(2):89-95, 1997.
Houchins, J.P. "DNA sequence analysis of NKG2, a family of related cDNA clones encoding type II integral membrane proteins on human natural killer cell" J. Exp. Med. 173:1017-1020, 1991.
Kubin, M. et al. "Molecular cloning and biological characterization of NK cell activation-inducing ligand, a counterstructure for CD48" Eur. J. Immunol. 29:3466-3477, 1999.
Lanier, L.L. "NK cell receptors" Annu. Rev. Immunol. 16:359-393, 1998.
Long, E.O. "Regulation of immune responses through inhibitory receptors" Annu. Rev. Immunol. 17:875-904, 1999.
Masucci, M.G. et al. "Down-regulation of class I HLA antigens and the Epstein-Barr virus-encoded latent membrane protein in Burkitt lymphoma lines" Proc. Natl. Acad. Sci. USA 84:4567-4571, 1987.
Matthew, P.A. et al. "Cloning an dcharacterization of the 2B4 gene encoding a molecule associated with non-MHC-restricted killing mediated by activated natural killer cells and T cells" J. Immunol. 151:5328-5337, 1993.
Mavaddat, N. et al. "Signaling lymphocytic activation molecule (CDw150) is homophilic but self-associates with very low affinity" J. Biol. Chem. 275(36):28100-28109, 2000.
Morra, M. et al. "X-linked lymphoproliferative disease: A progressive immunodeficiency" Annu. Rev. Immunol. 19:657-682, 2001.
Moretta, A. et al. "Novel surface molecules involved in human NK cell activation and triggering of the lytic machinery" Int. J. Cancer Suppl. 7:6-10, 1992.
Moretta, A. et al. "Receptors for HLA class-I molecules in human natural killer cells" Annu. Rev. Immunol. 14:619-648, 1996.
Moretta, A. et al. "Natural cytotoxicity receptors that trgger human NK-cell-mediated cytolysis" Immunol. Today 21:228-234, 2000.
Moretta, A. et al. "Activating receptors and coreceptors involved in human natural killer cell-mediated cytolysis" Annu. Rev. Immunol. 19:197-223, 2001.
Nakajima, H. et al. "Activating interations in human NK cell recognition: The role of 2B4-CD48" Eur. J. Immunol. 29:1676-1683, 1999.
Nakajima, H. et al. "Patients with X-linked lymphoproliferative disease have a defect in 2B4 receptor-mediated NK cell cytotoxicity" Eur. J. Immunol. 30:3309-3318, 2000.
Nichols, K.E. et al. "Inactivating mutations in an SH2 domain-encoding gene in X-linked lymphoproliferative syndrome" Proc. Natl. Acad. Sci. USA 95:13765-13770, 1998.
Parolini, S. et al. "X-linked lymphoproliferative diseasse: 2B4 molecules displaying inhibitory rather than activating function are responsible for the inability of natural killer cells to kill Epstein-Barr virus-infected cells" J. Exp. Med. 192(3):337-346, 2000.
Pende, D. et al. "Identification and molecular characterization of NKp30, a novel triggering receptor involved in natural cytotoxicity mediated by human natural killer cells" J. Exp. Med. 190(10:1505-1516, 1999.
Pende, D. et al. "Role of NKG2D in tumor cell lysis mediated by human NK cells: Cooperation with natural cytotoxicity receptors and capability of recognizing tumors of nonepithelial origin" Eur. J. Immunol. 31:1076-1086, 2001.
Pessino, A. et al. "Molecular cloning of NKp46: A novel member of the immunoglobulin superfamily involved in triggering of natural cytotoxicity" J. Exp. Med. 188(5):953-960, 1998.
Purtilo, D.T. "Fatal infectious mononucleosis in familial lymphohistiocytosis" N. Engl. J. Med. 201:736, 1974.
Rowe, M. et al. "Restoration of endogenous antigen processing in Burkitt's lymphoma cells by Epstein-Barr virus latent membrane protein-I: Coordinate up-regulation of peptide transporters and HLA-class I antigen expression" Eur. J. Immunol. 25:1374-1384, 1995.
Sayos, J. et al. "The X-linked lymphoproliferative-disease gene product SAP regulates signals induced through the co-receptor SLAM" Nature 395:462-469, 1998.
Seemayer, T.A. et al. X-linked lymphoproliferative disease : Twenty-five years after discovery >> Pediatric Res. 38(4):471-478, 1995.
Sivori, S. et al. "p46, a novel natural killer cell-specific surface molecule that mediates cell activation" J. Exp. Med. 186(7):1129-1136, 1997.
Sivori, S. et al. "NKp46 is the major triggering receptor involved in the natural cytotoxicity of fresh or cultured human NK cells. Correlation between surface density of NKp46 and natural cytotoxicity against autologous, allogeneic or xenogeneic target cells" Eur. J. Immunol. 29:1656-1666, 1999.
Sivori, S. et al. "2B4 functions as a co-receptor in human NK cells activation" Eur. J. Immunol. 30:787-793, 2000.
Tangye, S.G. et al. "Cutting edge: Human 2B4, an activating NK cell receptor, recruits the protein tyrosine phosphatase SHP-2 and the adaptor signaling protein SAP" J. Immunol. 162:6981-6985, 1999.
Tangye, S.G. et al. "The CD2-subset of the 1g superfamily of cell surface molecules: Receptor-ligand pairs expressed by NK cells and other immune cells" Immunology 12:149-157, 2000.
Tangye, S.G. et al. "Cutting edge: Functional requirement for SAP in 2B4-mediated activation of human natural killer cells as revealed bythe X-linked lymphoproliferative syndrome" J. Immunol. 165:2932-2936, 2000.
Tomasello, E. et al. "Signaling pathways engaged by NK cell receptors: Double concerto for activating receptors, inhibitory receptors and NK cells" Immunology 12:139-147, 2000.
Valiante, N.M. and G. Trinchieri. "Identification of a novel signal transduction surface molecule on human cytotoxic lymphocytes" J. Exp. Med. 178:1397-1406, 1993.
Vitale, M. et al. "NKp44, a novel triggering surface molecule specifically expressed by activated natural killer cells, is involved in non-major hsitocompatibility complex-restricted tumor cell lysis" J. Exp. Med. 187(12):2065-2072, 1998.
Wu, J. et al. "An activating immunoreceptor complex formed by NKG2D an dDAP10" Science 285:730-732, 1999.
Zeidler, R. et al. "Downregulation of TAP1 in B lymphocytes by cellular and Epstein-Barr virus-encoded intrleukin-10" Blood 90(6):2390-2397, 1997.
European Bioinformatics Institute EMBL-EBI FASTA Alignment Display Sequence Search Results for SEQ ID No. 2 in Uniprot Database, pp. 1-78.
European Bioinformatics Institute EMBL-EBI FASTA Alginment Display Sequence Search Results for SEQ ID No. 2 in JPOP, EPOP and USOPO Databases, pp. 1-42.
Dias Neto E., et al. Database EMBL Online, Ac No. AW851581, May 24, 2000, "IL3-CTO221-040400-107-D11 Homo sapiens CDNA, EST".
Pavitt, T. Database EMBL Online, Ac No. AL138932, Feb. 6, 2000, "Human DNA sequence from clone RP1-244G5".
Peck S.R. and H.E. Ruley. Database EMBL Online, Ac No. Q9ET40, Mar. 1, 2001, "Lymphocyte antigen 108 isoform L".

* cited by examiner

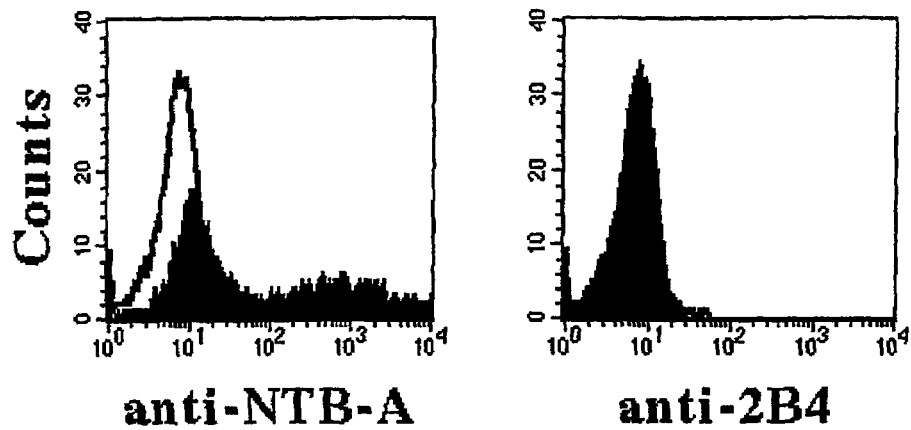

Figure 5 mlwlfqsllf vfcfgpgnvv sQSSLTPLMV NGILGESVTL PLEFPAGEKV NFITWLFNET 60
SLAFIVPHET KSPEIHVTNP KQGKRLNFTQ SYSLQLSNLK MEDTGSYRAQ ISTKTSAKLS 120
SYTLRILRQL RNIQVTNHSQ LFQNMTCELH LTCSVEDADD NVSFRWEALG NTLSSQPNLT 180
VSWDPRISSE QDYTCIAENA VSNLSFSVSA QKLCEDVKIQ YTDTKM ILFM VSGICIVFGF 240
IILLLLVL RK RRDSLSLSTQ RTQGPESARN LEYVSVSPTN NTVYASVTHS NRETEIWTPR 300
ENDTITIYST INHSKESKPT FSRATALDNV V 331

Figure 6A

```
ACCGCGGAAA GCATGTTGTG GCTGTTCCAA TCGCTCCTGT TTGTCTTCTG CTTTGGCCCA      60
           M  L  W  L  F  Q  S  L  L  F  V  C  F  G  P
GGGAATGTAG TTTCACAAAG CAGCTTAACC CCATTGATGG TGAACGGGAT TCTGGGGGAG     120
 G  N  V  V  S  Q  S  S  L  T  P  L  M  V  N  G  I  L  G  E
TCAGTAACTC TTCCCCTGGA GTTTCCTGCA GGAGAGAAGG TCAACTTCAT CACTTGGCTT     180
 S  V  T  L  P  L  E  F  P  A  G  E  K  V  N  F  I  T  W  L
TTCAATGAAA CATCTCTTGC CTTCATAGTA CCCCATGAAA CCAAAAGTCC AGAAATCCAC     240
 F  N  E  T  S  L  A  F  I  V  P  H  E  T  K  S  P  E  I  H
GTGACTAATC CGAAACAGGG AAAGCGACTG AACTTCACCC AGTCCTACTC CCTGCAACTC     300
 V  T  N  P  K  Q  G  K  R  L  N  F  T  Q  S  Y  S  L  Q  L
AGCAACCTGA AGATGGAAGA CACAGGCTCT TACAGAGCCC AGATATCCAC AAAGACCTCT     360
 S  N  L  K  M  E  D  T  G  S  Y  R  A  Q  I  S  T  K  T  S
GCAAAGCTGT CCAGTTACAC TCTGAGGATA TTAAGACAAC TGAGGAACAT ACAAGTTACC     420
 A  K  L  S  S  Y  T  L  R  I  L  R  Q  L  R  N  I  Q  V  T
AATCACAGTC AGCTATTTCA GAATATGACC TGTGAGCTCC ATCTGACTTG CTCTGTGGAG     480
 N  H  S  Q  L  F  Q  N  M  T  C  E  L  H  L  T  C  S  V  E
GATGCAGATG ACAATGTCTC ATTCAGATGG GAGGCCTTGG GAAACACACT TTCAAGTCAG     540
 D  A  D  D  N  V  S  F  R  W  E  A  L  G  N  T  L  S  S  Q
CCAAACCTCA CTGTCTCCTG GGACCCCAGG ATTTCCAGTG AACAGGACTA CACCTGCATA     600
 P  N  L  T  V  S  W  D  P  R  I  S  S  E  Q  D  Y  T  C  I
GCAGAGAATG CTGTCAGTAA TTTATCCTTC TCTGTCTCTG CCCAGAAGCT TGCGAAGAT      660
 A  E  N  A  V  S  N  L  S  F  S  V  S  A  Q  K  L  C  E  D
GTTAAAATTC AATATACAGA TACCAAAATG ATTCTGTTTA TGGTTTCTGG GATATGCATA     720
 V  K  I  Q  Y  T  D  T  K  M  I  L  F  M  V  S  G  I  C  I
GTCTTCGGTT TCATCATACT GCTGTTACTT GTTTTGAGGA AAAGAAGAGA TTCCCTATCT     780
 V  F  G  F  I  I  L  L  L  L  V  L  R  K  R  R  D  S  L  S
TTGTCTACTC AGCGAACACA GGGCCCCGAG TCCGCAAGGA ACCTAGAGTA TGTTTCAGTG     840
 L  S  T  Q  R  T  Q  G  P  E  S  A  R  N  L  E  Y  V  S  V
TCTCCAACCA ACAACACTGT GTATGCTTCA GTCACTCATT CAAACAGGGA AACAGAAATC     900
 S  P  T  N  N  T  V  Y  A  S  V  T  H  S  N  R  E  T  E  I
TGGACACCTA GAGAAAATGA TACTATCACA ATTTACTCCA CAATTAATCA TTCCAAAGAG     960
 W  T  P  R  E  N  D  T  I  T  I  Y  S  T  I  N  H  S  K  E
AGTAAACCCA CTTTTTCCAG GGCAACTGCC CTTGACAATG TCGTGTAAGT TGCTGAAAGG    1020
 S  K  P  T  F  S  R  A  T  A  L  D  N  V  V  *
CCTCAGAGGA ATTCGGGAAT GACACGTCTT CTGATCCCAT GAGACAGAAC AAAGAACAGG    1080

AAGCTTGGTT CCTGTTGTTC CTGGCAACAG AATTTGAATA TCTAGGATAG GATGATCACC    1140

TCCAGTCCTT CGGACTTAAA CCTGCCTACC TGAGTCAAAC ACCTAAGGAT AACATCATTT    1200

CCAGCATGTG GTTCAAATAA TATTTTCCAA TCCACTTCAG GCCAAAACAT GCTAAAGATA    1260

ACACACCAGC ACATTGACTC TCTCTTTGAT AACTAAGCAA ATGGAATTAT GGTTGACAGA    1320

GAGTTTATGA TCCAGAAGAC AACCACTTCT CTCCTNNTAG AAAGCAGCAG GATTGACTTA    1380

TTGAGAAATA ATGCAGTGTG TTGTTACAT GTGTAGTCTC TGGAGTTGGA TGGGCCCATC     1440

CTGATACAAG TTGAGCATCC CTTGTCTGAA ATGCTTGGGA TTAGAAATGT TTCAGATTTC    1500

AATTTTTTTT CAGATTTTGG AATATTTGCA TTATATTTAG CGGTTGAGTA TCCAAATCCA    1560

AAAATCCAAA ATTCAAAATG CTCCAATAAG CATTTCCCTT GAGTTTCATT GATGTCGATG    1620

CAGTGCTCAA AATCTCAGAT TTTGGAGCAT TTTGGATATT GGATTTTTGG ATTTGGGATG    1680

CTCAACTTGT ACAATGTTTA TTAGACACAT CTCCTGGGAC ATACTGCCTA ACCTTTTGGA    1740

GCCTTAGTCT CCCAGACTGA AAAAGGAAGA GGATGGTATT ACATCAGCTC CATTGTTTGA    1800

GCCAAGAATC TAAGTCATCC CTGACTCCAG TGTCTTTGTC ACCAGGCCCT TTGGACTCTA    1860

CCTCAGAAAT ATTTCTTGGA CCTTCCACTT CTCCTCCAAC TCCTTGACCA CCATCCTGTA    1920

TCCAACCATC ACCACCTCTA ACCTGAATCC TACCTTAAGA TCAGAACAGT TGTCCTCACT    1980

TTTGTTCTTG TCCCTCTCCA ACCCACTCTC CACAAGATGG CCAGAGTAAT GTTTTTAATA    2040

TAAATTGGAT CCTTCAGTTT CCTGCTTAAA ACCCTGCAGG TTTCCCAATG CACTCAGAAA    2100

GAAATCCAGT TTTCATGGCC CTGGATGGTC TGGCCCACCT CCAGCCTCAG CTAGCATTAC    2160

CCTTCTGACA CTCTCTATGT AGCCTCCCTG ATCTTCTTTC AGCTCCTCTA TTAAAGGAAA    2220

AGTTCTTTAT GTTAATTATT TACATCTTCC TGCAGGCCCT TCCTCTGCCT GCTGGGGTCC    2280

TCCTATTCTT TAGGTTTAAT TTTAAATATG TCACCTCCTA AGAGAAACCT TCCCAGACCA    2340

CTCTTTCTAA AATGAATCTT CTAGGCTGGG CATGGTGGCT CACACCTGTA ATCCCAGTAC    2400

TTTGGGAGGC CAAGGGGGGA GATCACTTGA GGTCAGGAGT TCAAGCCCAG CCTGGCCCAC    2460

TTGGTTAAAC CCCGTYTTTT YTWAAAATAC AAAAAAATTA GCCMGGSSKG GKGGKGCCCC    2520

CCTAAAATCC CAGCTCCTTT ARAGAYTNAG GCAGGARAAT CCCTTKAACC CAGGAGGKGG    2580

RGGTTCCAKT KAGCCAAAAT CATGCCAATG TWTTCCMGTT TGGGKGRCAA ARTRARACTY    2640

TGTYYCCAAA AATWAATTAA TTAAATWAAA TKAAATTGTT TTTTAAAAA AAAAAAAAAA    2700

AAAAAAAAAA AAAAAAAAAA AAAAAAAA                                       2728
```

Figure 6B

SEQUENCE LISTING

<160> NUMBER OF SEQ ID NOS: 4

<210> SEQ ID NO 1
<211> LENGTH: 2728
<212> TYPE: DNA
<213> ORGANISM: Artificial Sequence
<220> FEATURE:
<223> OTHER INFORMATION: Description of Artificial Sequence: Amino acid
      sequence of SF-1.
<220> FEATURE:
<221> NAME/KEY: CDS
<222> LOCATION: (13)..(1005)
<220> FEATURE:
<221> NAME/KEY: misc_feature
<222> LOCATION: (1356)..(1357)
<223> OTHER INFORMATION: n = G or A or T or C
<220> FEATURE:
<221> NAME/KEY: misc_feature
<222> LOCATION: (2476)..(2476)
<223> OTHER INFORMATION: y = T or C
<220> FEATURE:
<221> NAME/KEY: misc_feature
<222> LOCATION: (2481)..(2481)
<223> OTHER INFORMATION: y = T or C
<220> FEATURE:
<221> NAME/KEY: misc_feature
<222> LOCATION: (2483)..(2483)
<223> OTHER INFORMATION: w = A or T
<220> FEATURE:
<221> NAME/KEY: misc_feature
<222> LOCATION: (2504)..(2504)
<223> OTHER INFORMATION: m = A or C
<220> FEATURE:
<221> NAME/KEY: misc_feature
<222> LOCATION: (2507)..(2508)
<223> OTHER INFORMATION: s = G or C
<220> FEATURE:
<221> NAME/KEY: misc_feature
<222> LOCATION: (2509)..(2509)
<223> OTHER INFORMATION: k = G or T
<220> FEATURE:
<221> NAME/KEY: misc_feature
<222> LOCATION: (2512)..(2512)
<223> OTHER INFORMATION: k = G or T
<220> FEATURE:
<221> NAME/KEY: misc_feature
<222> LOCATION: (2515)..(2515)
<223> OTHER INFORMATION: k = G or T
<220> FEATURE:
<221> NAME/KEY: misc_feature
<222> LOCATION: (2542)..(2542)
<223> OTHER INFORMATION: r = G or A
<220> FEATURE:
<221> NAME/KEY: misc_feature
<222> LOCATION: (2546)..(2546)
<223> OTHER INFORMATION: y = T or C
<220> FEATURE:
<221> NAME/KEY: misc_feature
<222> LOCATION: (2548)..(2548)
<223> OTHER INFORMATION: n = G or A or T or C
<220> FEATURE:
<221> NAME/KEY: misc_feature
<222> LOCATION: (2557)..(2557)
<223> OTHER INFORMATION: r = G or A
<220> FEATURE:
<221> NAME/KEY: misc_feature
<222> LOCATION: (2566)..(2566)
<223> OTHER INFORMATION: k = G or T
<220> FEATURE:
<221> NAME/KEY: misc_feature
<222> LOCATION: (2578)..(2578)
<223> OTHER INFORMATION: k = G or T
<220> FEATURE:
<221> NAME/KEY: misc_feature
<222> LOCATION: (2581)..(2581)
<223> OTHER INFORMATION: r = G or A
<220> FEATURE:
<221> NAME/KEY: misc_feature
<222> LOCATION: (2589)..(2589)
<223> OTHER INFORMATION: k = G or T
<220> FEATURE:
<221> NAME/KEY: misc_feature
<222> LOCATION: (2591)..(2591)
<223> OTHER INFORMATION: k = G or T
<220> FEATURE:
<221> NAME/KEY: misc_feature
<222> LOCATION: (2612)..(2612)
<223> OTHER INFORMATION: w = A or T
<220> FEATURE:
<221> NAME/KEY: misc_feature
<222> LOCATION: (2617)..(2617)
<223> OTHER INFORMATION: m = A or C
<220> FEATURE:
<221> NAME/KEY: misc_feature
<222> LOCATION: (2625)..(2625)
<223> OTHER INFORMATION: k = G or T
<220> FEATURE:
<221> NAME/KEY: misc_feature
<222> LOCATION: (2627)..(2627)
<223> OTHER INFORMATION: r = G or A
<220> FEATURE:
<221> NAME/KEY: misc_feature
<222> LOCATION: (2632)..(2632)
<223> OTHER INFORMATION: r = G or A
<220> FEATURE:
<221> NAME/KEY: misc_feature
<222> LOCATION: (2634)..(2634)
<223> OTHER INFORMATION: r = G or A
<220> FEATURE:
<221> NAME/KEY: misc_feature
<222> LOCATION: (2636)..(2636)
<223> OTHER INFORMATION: r = G or A
<220> FEATURE:
<221> NAME/KEY: misc_feature
<222> LOCATION: (2640)..(2640)
<223> OTHER INFORMATION: y = T or C
<220> FEATURE:
<221> NAME/KEY: misc_feature
<222> LOCATION: (2644)..(2645)
<223> OTHER INFORMATION: y = T or C
<220> FEATURE:
<221> NAME/KEY: misc_feature
<222> LOCATION: (2654)..(2654)
<223> OTHER INFORMATION: w = A or T
<220> FEATURE:
<221> NAME/KEY: misc_feature
<222> LOCATION: (2667)..(2667)
<223> OTHER INFORMATION: w = A or T
<220> FEATURE:
<221> NAME/KEY: misc_feature
<222> LOCATION: (2672)..(2672)
<223> OTHER INFORMATION: k = G or T

<400> SEQUENCE: 1

```
accgcggaaa gc atg ttg tgg ctg ttc caa tcg ctc ctg ttt gtc ttc tgc      51
              Met Leu Trp Leu Phe Gln Ser Leu Leu Phe Val Phe Cys
                1               5                   10 ttt ggc cca ggg aat gta gtt tca caa agc agc tta acc cca ttg atg        99
Phe Gly Pro Gly Asn Val Val Ser Gln Ser Ser Leu Thr Pro Leu Met
 15                  20                  25 gtg aac ggg att ctg ggg gag tca gta act ctt ccc ctg gag ttt cct       147
Val Asn Gly Ile Leu Gly Glu Ser Val Thr Leu Pro Leu Glu Phe Pro
 30                  35                  40                  45 gca gga gag aag gtc aac ttc atc act tgg ctt ttc aat gaa aca tct       195
Ala Gly Glu Lys Val Asn Phe Ile Thr Trp Leu Phe Asn Glu Thr Ser
                 50                  55                  60 ctt gcc ttc ata gta ccc cat gaa acc aaa agt cca gaa atc cac gtg       243
Leu Ala Phe Ile Val Pro His Glu Thr Lys Ser Pro Glu Ile His Val
             65                  70                  75
```

```
act aat ccg aaa cag gga aag cga ctg aac ttc acc cag tcc tac tcc     291
Thr Asn Pro Lys Gln Gly Lys Arg Leu Asn Phe Thr Gln Ser Tyr Ser
        80                  85                  90 ctg caa ctc agc aac ctg aag atg gaa gac aca ggc tct tac aga gcc     339
Leu Gln Leu Ser Asn Leu Lys Met Glu Asp Thr Gly Ser Tyr Arg Ala
 95                 100                 105 cag ata tcc aca aag acc tct gca aag ctg tcc agt tac act ctg agg     387
Gln Ile Ser Thr Lys Thr Ser Ala Lys Leu Ser Ser Tyr Thr Leu Arg
110             115                 120                 125 ata tta aga caa ctg agg aac ata caa gtt acc aat cac agt cag cta     435
Ile Leu Arg Gln Leu Arg Asn Ile Gln Val Thr Asn His Ser Gln Leu
                130                 135                 140 ttt cag aat atg acc tgt gag ctc cat ctg act tgc tct gtg gag gat     483
Phe Gln Asn Met Thr Cys Glu Leu His Leu Thr Cys Ser Val Glu Asp
            145                 150                 155 gca gat gac aat gtc tca ttc aga tgg gag gcc ttg gga aac aca ctt     531
Ala Asp Asp Asn Val Ser Phe Arg Trp Glu Ala Leu Gly Asn Thr Leu
        160                 165                 170 tca agt cag cca aac ctc act gtc tcc tgg gac ccc agg att tcc agt     579
Ser Ser Gln Pro Asn Leu Thr Val Ser Trp Asp Pro Arg Ile Ser Ser
175                 180                 185 gaa cag gac tac acc tgc ata gca gag aat gct gtc agt aat tta tcc     627
Glu Gln Asp Tyr Thr Cys Ile Ala Glu Asn Ala Val Ser Asn Leu Ser
190                 195                 200                 205 ttc tct gtc tct gcc cag aag ctt tgc gaa gat gtt aaa att caa tat     675
Phe Ser Val Ser Ala Gln Lys Leu Cys Glu Asp Val Lys Ile Gln Tyr
                210                 215                 220 aca gat acc aaa atg att ctg ttt atg gtt tct ggg ata tgc ata gtc     723
Thr Asp Thr Lys Met Ile Leu Phe Met Val Ser Gly Ile Cys Ile Val
            225                 230                 235 ttc ggt ttc atc ata ctg ctg tta ctt gtt ttg agg aaa aga aga gat     771
Phe Gly Phe Ile Ile Leu Leu Leu Val Leu Arg Lys Arg Arg Asp
        240                 245                 250 tcc cta tct ttg tct act cag cga aca cag ggc ccc gag tcc gca agg     819
Ser Leu Ser Leu Ser Thr Gln Arg Thr Gln Gly Pro Glu Ser Ala Arg
255                 260                 265 aac cta gag tat gtt tca gtg tct cca acg aac aac act gtg tat gct     867
Asn Leu Glu Tyr Val Ser Val Ser Pro Thr Asn Asn Thr Val Tyr Ala
270                 275                 280                 285 tca gtc act cat tca aac agg gaa aca gaa atc tgg aca cct aga gaa     915
Ser Val Thr His Ser Asn Arg Glu Thr Glu Ile Trp Thr Pro Arg Glu
                290                 295                 300 aat gat act atc aca att tac tcc aca att aat cat tcc aaa gag agt     963
Asn Asp Thr Ile Thr Ile Tyr Ser Thr Ile Asn His Ser Lys Glu Ser
            305                 310                 315 aaa ccc act ttt tcc agg gca act gcc ctt gac aat gtc gtg            1005
Lys Pro Thr Phe Ser Arg Ala Thr Ala Leu Asp Asn Val Val
                320                 325                 330 taagttgctg aaaggcctca gaggaattcg ggaatgacac gtcttctgat cccatgagac    1065
agaacaaaga acaggaagct tggttcctgt tgttcctggc aacagaattt gaatatctag    1125
gataggatga tcacctccag tccttcggac ttaaacctgc ctacctgagt caaacaccta    1185
aggataacat catttccagc atgtggttca ataatatttt tccaatccac ttcaggccaa    1245
aacatgctaa agataacaca ccagcacatt gactctctct tgataacta agcaaatgga    1305 attatggttg acagagagtt tatgatccag aagacaacca cttctctcct nntagaaagc    1365
agcaggattg acttattgag aaataatgca gtgtgttggt tacatgtgta gtctctggag    1425
ttggatgggc ccatcctgat acaagttgag catcccttgt ctgaaatgct tgggattaga    1485
```

-continued

```
aatgtttcag atttcaattt ttttcagat tttggaatat ttgcattata tttagcggtt    1545
gagtatccaa atccaaaaat ccaaaattca aaatgctcca ataagcattt cccttgagtt    1605
tcattgatgt cgatgcagtg ctcaaaatct cagattttgg agcattttgg atattggatt    1665
tttggatttg ggatgctcaa cttgtacaat gtttattaga cacatctcct gggacatact    1725
gcctaacctt ttggagcctt agtctcccag actgaaaaag gaagaggatg gtattacatc    1785
agctccattg tttgagccaa gaatctaagt catccctgac tccagtgtct tgtcaccag     1845 gcccttttgga ctctacctca gaaatatttc ttggaccttc cacttctcct ccaactcctt   1905
gaccaccatc ctgtatccaa ccatcaccac ctctaacctg aatcctacct taagatcaga   1965
acagttgtcc tcacttttgt tcttgtccct ctccaaccca ctctccacaa gatggccaga   2025
gtaatgtttt taatataaat tggatccttc agtttcctgc ttaaaaccct gcaggtttcc   2085
caatgcactc agaaagaaat ccagttttca tggccctgga tggtctggcc cacctccagc   2145
ctcagctagc attacccttc tgacactctc tatgtagcct ccctgatctt ctttcagctc   2205
ctctattaaa ggaaaagttc tttatgttaa ttatttacat cttcctgcag gcccttcctc   2265
tgcctgctgg ggtcctccta ttctttaggt ttaatttaa atatgtcacc tcctaagaga    2325
aaccttccca gaccactctt tctaaaatga atcttctagg ctgggcatgg tggctcacac   2385
ctgtaatccc agtactttgg gaggccaagg ggggagatca cttgaggtca ggagttcaag   2445
cccagcctgg cccacttggt taaaccccgt yttttytwaa aatacaaaaa aattagccmg   2505
gsskggkggk gccccctaa aatcccagct cctttaraga ytnaggcagg araatccctt    2565
kaacccagga ggkggrggtt ccaktkagcc aaaatcatgc caatgtwttc cmgtttgggk   2625
grcaaartra ractytgtyy ccaaaaatwa attaattaaa twaaatkaaa ttgttttttt   2685
aaaaaaaaaa aaaaaaaaaa aaaaaaaaaa aaaaaaaaaa aaa                     2728
```

<210> SEQ ID NO 2
<211> LENGTH: 331
<212> TYPE: PRT
<213> ORGANISM: Artificial Sequence
<220> FEATURE:
<223> OTHER INFORMATION: Synthetic Construct

<400> SEQUENCE: 2

```
Met Leu Trp Leu Phe Gln Ser Leu Leu Phe Val Phe Cys Phe Gly Pro
1               5                   10                  15

Gly Asn Val Val Ser Gln Ser Ser Leu Thr Pro Leu Met Val Asn Gly
            20                  25                  30

Ile Leu Gly Glu Ser Val Thr Leu Pro Leu Glu Phe Pro Ala Gly Glu
        35                  40                  45

Lys Val Asn Phe Ile Thr Trp Leu Phe Asn Glu Thr Ser Leu Ala Phe
    50                  55                  60

Ile Val Pro His Glu Thr Lys Ser Pro Glu Ile His Val Thr Asn Pro
65                  70                  75                  80

Lys Gln Gly Lys Arg Leu Asn Phe Thr Gln Ser Tyr Ser Leu Gln Leu
                85                  90                  95

Ser Asn Leu Lys Met Glu Asp Thr Gly Ser Tyr Arg Ala Gln Ile Ser
            100                 105                 110

Thr Lys Thr Ser Ala Lys Leu Ser Ser Tyr Thr Leu Arg Ile Leu Arg
        115                 120                 125

Gln Leu Arg Asn Ile Gln Val Thr Asn His Ser Gln Leu Phe Gln Asn
    130                 135                 140
```

```
Met Thr Cys Glu Leu His Leu Thr Cys Ser Val Glu Asp Ala Asp Asp
145                 150                 155                 160

Asn Val Ser Phe Arg Trp Glu Ala Leu Gly Asn Thr Leu Ser Ser Gln
                165                 170                 175

Pro Asn Leu Thr Val Ser Trp Asp Pro Arg Ile Ser Ser Glu Gln Asp
            180                 185                 190

Tyr Thr Cys Ile Ala Glu Asn Ala Val Ser Asn Leu Ser Phe Ser Val
        195                 200                 205

Ser Ala Gln Lys Leu Cys Glu Asp Val Lys Ile Gln Tyr Thr Asp Thr
    210                 215                 220

Lys Met Ile Leu Phe Met Val Ser Gly Ile Cys Ile Val Phe Gly Phe
225                 230                 235                 240

Ile Ile Leu Leu Leu Val Leu Arg Lys Arg Arg Asp Ser Leu Ser
                245                 250                 255

Leu Ser Thr Gln Arg Thr Gln Gly Pro Glu Ser Ala Arg Asn Leu Glu
            260                 265                 270

Tyr Val Ser Val Ser Pro Thr Asn Asn Thr Val Tyr Ala Ser Val Thr
        275                 280                 285

His Ser Asn Arg Glu Thr Glu Ile Trp Thr Pro Arg Glu Asn Asp Thr
    290                 295                 300

Ile Thr Ile Tyr Ser Thr Ile Asn His Ser Lys Glu Ser Lys Pro Thr
305                 310                 315                 320

Phe Ser Arg Ala Thr Ala Leu Asp Asn Val Val
                325                 330

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer
      KALI-up.

<400> SEQUENCE: 3
gcggaaagca tgttgtgg                                                    18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Primer
      KALI-down.

<400> SEQUENCE: 4
tcattcccga attcctctg                                                   19
```

NTB-A, A SURFACE MOLECULE INVOLVED IN NATURAL KILLER CELLS ACTIVITY

This application is the U.S. national stage application of International patent application No. PCT/EP02/07945, filed Jul. 17, 2002, which claims the benefit of application EP 01401946.7, filed Jul. 19, 2001.

The present invention relates to a novel protein, termed NTB-A, nucleic acid molecules encoding the same and uses thereof. The invention also relates to methods of regulating an immune response in a subject by regulating the activity of NTB-A in vitro, ex vivo or in vivo. The invention also relates to methods of regulating the activity of immune cells, particularly of Natural Killer cells, T lymphocytes and/or B lymphocytes by regulating the activity of NTB-A in vitro, ex vivo or in vivo The invention also comprises methods of screening active compounds using NTB-A or fragments thereof, or nucleic acid encoding the same, or recombinant host cells expressing said polypeptide.

Important advances have recently been made in our understanding of the role of human NK cells in host defenses. Progress is mainly consequent to the discovery of a series of receptors, expressed at the NK cell surface, regulating NK cell functions. Some of these receptors inhibit NK cells by monitoring the expression of MHC class I molecules on normal cells (1–3). Other receptors are responsible for NK cell activation (4). This occurs when NK cells interact with cells that, as a consequence of viral infection or tumor transformation, do not express, or express inadequate amounts of, MHC class I molecules (5). In humans, different triggering receptors have been identified. NKp46 (6,7), NKp30 (8), and NKp44 (9, 10), collectively termed "natural cytotoxicity receptors" (NCRs) (11) are selectively expressed by NK cells and cooperate with each other in the induction of natural cytotoxicity. NCRs are characterized by a coordinated surface expression and a direct correlation exists between their surface density and the ability of NK cells to kill various tumors (12). NCRs are all members of the Ig superfamily (IG-SF), display low degree of similarity to each other, and are coupled to different signal transducing adaptor proteins including CD3ζ, FcεRIγ, and KARAP/DAP12 (8–10).

Another triggering receptor expressed by NK cells is represented by NKG2D, a C-type lectin surface molecule encoded within the "NK gene complex" on human chromosome12 (13). Upon recognition of the stress-inducible MICA/B molecules (14) on target cells, NKG2D strongly enhances the NK-mediated cytotoxicity (14, 15). Different from NCR, NKG2D is also expressed by virtually all TCR-γ/δ+ as well as by CD8 TCR-α/β+ cells. Its function requires the association with a newly identified signalling subunit termed DAP10 (16) or KAP10 (17). As recently shown, NKG2D can complement the role of NCRs in tumor cell lysis, their relative involvement being primarily dependent on the type of target and/or effector cells analyzed (15).

Notably, optimal NK cell triggering may require the function of another molecule termed 2B4 (CD244; references 18–20). This molecule is expressed not only by NK cells, but also by monocytes and a subset of CD8 T cells. InNK cells, the mAb-mediated cross-linking of 2B4 or its engagement by CD48 (i.e., the 2B4 ligand) results in the enhancement of cytolytic activity (18–22). Analysis at the clonal level has clearly shown that this effect is restricted to NK cells expressing high NCR surface density (NCR bright). Moreover, mAb-mediated modulation of NCRs results in NK cell unresponsiveness to 2B4 engagement, although its surface expression is not affected. Thus, the ability of 2B4 to induce NK cell activation appears to be dependent on the co-engagement of main triggering receptors including NKp46. This supports the notion that 2B4 may function as a co-receptor rather than as a true receptor (23). 2B4 is a member of the CD2 subfamily of the Ig-SF which also includes CD48, CD58, CD84, CD150 (also termed SLAM), and CD299 (Ly9) (24). 2B4 is characterized, in its extracellular portion, by a membrane-distal Ig V domain and a membrane-proximal IgC2 domain. The transmembrane region lacks charged amino acids involved in the association with immune tyrosine-based activating motif (ITAM)-bearing signal transducing polypeptides (21, 22, 25–27). Interestingly, the cytoplasmic tail contains four tyrosine-based motifs (TxYxxI/V) that undergo phosphorylation upon sodium pervanadate treatment (27, 28) or cell triggering with anti-2B4 mAb (29). Different polypeptides have been shown to associate with 2B4 and to participate in the 2B4-mediated signal transduction pathway. Thus, upon tyrosine phosphorylation, 2B4 associates with a small cytoplasmic polypeptide termed Src homology 2 domain-containing protein (SH2D1A; references 27 and 28) also referred to as SLAM-associated protein (SAP [30]). Controversy still exists on which of the SH2-containing phosphatases (SHP) binds to 2B4. Although 2B4/SHP-2 association has been described in cell transfectants (27), in normal NK cells, only 2B4/SHP-1-association could be detected (28). Recently, it has been shown that, in normal NK cells, 2B4 constitutively associates with the linker for activation of T cells (LAT [29]). mAb-mediated cross-linking of 2B4 results in tyrosine phosphorylation of LAT and recruitment of PLCγ and Grb2 intracytoplasmic signalling molecules (29).

A dramatically altered function of 2B4 has recently been detected in individuals affected by the X-linked lymphoproliferative disease (XLP [28, 31, 32]). XLP is a severe inherited immune deficiency, characterized by the inability to control EBV infection resulting in fulminant infectious mononucleosis or lymphoma (33, 34). The genetic basis of XLP, i.e., critical mutations in the SH2D1A encoding gene (30, 35, 36) has been identified. Due to these mutations, in XLP-NK cells 2B4 fails to associate with SH2D1A but associates with SHP-1 and mediates inhibitory (rather than activating) signals (28). Thus, the engagement of 2B4 with CD48 expressed at high densities on EBV-infected cells results in a sharp inhibition of the NK-mediated cytotoxicity.

The present invention stems from the identification, cloning and functional characterization of a novel NK cells surface molecule, termed NTB-A.

NTB-A, a 60-kD glycoprotein, is expressed by human NK, T, and B lymphocytes. Monoclonal antibody (mAb)-mediated cross-linking of NTB-A results in the induction of NK-mediated cytotoxicity. Similar to 2B4 (CD244) functioning as a co-receptor in the NK cell activation, NTB-A also triggers cytolytic activity only in NK cells expressing high surface densities of natural cytotoxicity receptors. This indicates that NTB-A may function as a co-receptor in the process of NK cell activation. Molecular cloning of the cDNA coding for NTB-A molecule revealed a novel member of the immunoglobulin superfamily belonging to the CD2 subfamily. NTB-A is characterized, in its extracellular portion, by a distal V-type and a proximal C2-type domain and by a cytoplasmic portion containing three tyrosine-based motifs. NTB-A undergoes tyrosine phosphorylation and associates with the Src homology 2 domain-containing protein (SH2D1A) as well as with SH2 domain-containing phosphatases (SHPs). Importantly, analysis of NK cells derived from patients with X-linked lymphoproliferative disease (XLP) showed that the lack of SH2D1A protein profoundly affects the function not only of 2B4 but also of NTB-A. Thus, in XLP-NK cells, NTB-A mediates inhibitory rather than activating signals. These inhibitory signals are induced by the interaction of NTB-A with still undefined ligands expressed on Epstein-Barr virus (EBV)-infected target cells. Moreover, mAb-mediated masking of NTB-A can partially revert this inhibitory effect while a maximal recovery of target cell lysis can be obtained when both 2B4 and NTB-A are simultaneously masked. Thus, the altered function of NTB-A appears to play an important role in the inability of XLP-NK cells to kill EBV-infected target cells.

An object of this invention resides in a nucleic acid molecule encoding a NTB-A polypeptide.

A farther aspect of this invention resides in an isolated NTB-A polypeptide.

A further aspect of this invention is an antibody that binds a NTB-A polypeptide.

Still a further aspect of this invention is a method of regulating an immune response in a subject comprising administering to the subject a compound that regulates the activity of NTB-A.

The invention also relates to methods of screening compounds comprising determining the ability of a test compound to regulate the activity of NTB-A.

The invention also relates to a pharmaceutical composition comprising a compound that regulates the activity of NTB-A and a pharmaceutically acceptable vehicle or carrier.

The invention also relates to methods of diagnosing a dysfunction in a subject, comprising determining the presence of a mutation or alteration in a NTB-A gene or RNA, or determining the presence or amount of a NTB-A polypeptide.

The invention is particularly suited to treat or diagnose pathologies in which the activity of immune cells is involved, particularly NK cells, T cells and/or B cells. The invention is particularly suited to treat or diagnose pathologies in which the activity of NK cells is involved such as viral infections, tumor or other proliferative diseases, autoimmune diseases, etc. The invention can be used, by way of example, to treat patients with X-linked lymphoproliferative disease.

Nucleic Acid Molecules

A particular aspect of this invention is a nucleic acid molecule selected from:
  a) a nucleic acid encoding a polypeptide comprising amino acid sequence SEQ ID NO:2;
  b) a nucleic acid which hybridises to the nucleic acid a) or to a portion thereof, said portion comprising at least 30 contiguous nucleotides of a nucleic acid a),
  c) a complementary strand of a nucleic acid molecule of a) or b), and
  d) a fragment of a nucleic acid molecule of a), b) or c), said fragment comprising at least 9 contiguous nucleotides.

In a particular embodiment, the invention relates to a nucleic acid molecule comprising a sequence encoding a polypeptide comprising amino acid sequence SEQ ID NO:2 or a polypeptide comprising at least 5 contiguous amino acid residues of SEQ ID NO:2.

The invention particularly encompasses any nucleic acid molecule encoding a human NTB-A protein or polypeptide, as defined above.

The nucleic acid molecule can be a DNA or a RNA molecule. It can be a gDNA, cDNA or a synthetic or semi-synthetic DNA, e.g., comprising added sequences such as introns, biased codons, etc. The nucleic acid may be prepared by any conventional technique, such as by artificial synthesis, cloning, or combinations thereof.

A preferred, specific embodiment is a nucleic acid comprising SEQ ID NO:1 or a portion thereof comprising at least 9 contiguous nucleotides thereof, or a complementary strand thereof.

As indicated, the invention encompasses nucleic acid molecules that hybridises to a nucleic acid encoding a polypeptide comprising amino acid sequence SEQ ID NO:2, or to a portion thereof, said portion comprising at least 30 contiguous nucleotides of a nucleic acid. Hybridization can be performed either under stringent or non-stringent conditions, preferably under stringent conditions. Typically, encompassed nucleic acids are those hybridising to the above sequences under the following conditions: incubation at 42° C. in 50% formamide, 5×SSPE, 5× Denhardt's solution, 0.1% SDS (1×SSPE is composed of 0.15M NaCl, 10 mM $NaH_2PO_4$, 1.3 mM EDTA, pH 7.4). Stringent conditions are also described in ref. 37. The nucleic acid should hybridize to the entire coding sequence or, as indicated, to at least a portion thereof comprising 30 contiguous nucleotides. It is believed that such a length ensures high specificity of hybridization. The hybridizing nucleic acid preferably encodes a polypeptide having a receptor function, or a part thereof.

Preferred fragments d) of the above nucleic acid molecules comprise at least 15 contiguous nucleotides, even more preferably at least 21 nucleotides.

The above nucleic acid molecules may be used to produce a NTB-A polypeptide in vitro, ex vivo or in vivo, to amplify the nucleic acid in any appropriate cell, as a probe or as a primer, for instance. These nucleic acids may also be used as antisense molecules (or to design antisense molecules) to regulate NTB-A expression in a cell, in vitro, ex vivo or in vivo.

In this respect, an object of this invention resides in a nucleic acid probe, wherein said probe is complementary and specifically hybridizes to a nucleic acid molecule as defined above. The probe is preferably a single-strand molecule, comprising, preferably, from 9 to about 300 nucleotides. The probe may comprise the full nucleic acid sequence encoding a NTB-A polypeptide. The probe can be specific for variants, mutants or deletants and specifically detect such species in a sample. The probe may be labelled, by any conventional means such as radioactive, enzymatic, fluorescent, luminescent, chemical, etc. The probe can be used to detect the presence of a NTB-A gene or RNA in a sample, particularly the presence of a mutation or alteration in a NTB-A gene or RNA in a sample.

The invention also encompasses a pair of nucleic acid primers, wherein at least one primer of said pair is complementary and specifically hybridizes to a nucleic acid molecule as defined above. Such a pair of primer can be used to amplify, in a sample, all or part of a gene or RNA coding for NTB-A. Amplification can be performed by PCR, as described in the examples, or by any other known technique. The primer is preferably a single-stranded nucleic acid molecule of less than about 50 nucleotides in length, typically of between 10–50 nucleotides in length.

An antisense molecule is any nucleic acid that specifically hybridises to a NTB-A gene or RNA and prevents or reduces transcription or translation thereof. The antisense may be DNA or RNA, single- or double-stranded, and preferably comprises a portion of a nucleic acid sequence as described above, typically at least 30 nucleotides thereof.

Vectors

The invention relates to any vector comprising a nucleic acid molecule as defined above. The vector may be any plasmid, phage, episome, artificial chromosome, virus, etc. Typical examples include plasmid vectors, such as those derived from commercially available plasmids (pUC, pBR322, pcDNA, etc.). Other preferred vectors are viruses, particularly recombinant (replication-defective) viruses, such as those derived from retroviruses, baculoviruses, lentiviruses, AAVs, adenoviruses, herpesviruses, etc. The vectors can be prepared by conventional techniques, e.g., by ligating the NTB-A nucleic acid molecule into appropriate cloning site of the vector. The vector may further comprise regulatory sequences, such as promoters, terminators, enhancers, silencers, etc., origin(s) of replication, marker genes, etc. Typical examples of promoters include promoters allowing constitutive or regulated or tissue-selective expression, weak or strong promoters, of cellular, viral or synthetic origin, such as RVS-LTR, SV40-IE, CMV-IE promoter, promoters of domestic genes (PGK, etc.), promoters of bacteria or phage (T7, Lac, Trp, etc.), etc.

The vectors can be used to express a nucleic acid of this invention in vitro, ex vivo or in vivo. In particular, the vectors can be used to produce a NTB-A polypeptide in a cell, in vitro or ex vivo, as well as directly in vivo, in a gene therapy program.

Polypeptides

An other object of this invention is a NTB-A polypeptide. Within the context of the present invention, a NTB-A polypeptide designates any polypeptide comprising SEQ ID NO:2, as well as any variants, derivatives or homologs thereof, including any naturally-occurring derivatives thereof or homologs isolated from various mammalian species (including rodents, equine, bovine, etc.). Variants more generally encompass any polypeptide having one or several amino acid modifications as compared to SEQ ID NO:2, including mutation(s), deletion(s), insertion(s) and/or substitution(s), alone or in various combinations(s). More preferably, a NTB-A polypeptide is a polypeptide having at least 70% identity, more preferably at least 80%, further preferably at least 90% identity with the amino acid sequence of SEQ ID NO: 2 or to a fragment thereof. Identity can be determined using known methods and commercial computer programs, such as CLUSTAL or BLAST (NCBI). Various search or alignment parameters may also be used. In a preferred embodiment, percentage amino acid (or nucleic acid) identity is determined using the CLUSTAL-W program (Compugen).

In a specific embodiment, the invention relates to a polypeptide comprising amino acid sequence SEQ ID NO:2 or a fragment thereof comprising at least 5 contiguous amino acid residues of SEQ ID NO:2.

In an other specific embodiment, this invention relates to a polypeptide comprising amino acid sequence SEQ ID NO:2 having an extra alanine residue at position 266, or a fragment thereof comprising at least 5 contiguous amino acid residues. The inventors have indeed identified an allelic isoform of NTB-A comprising an extra codon (CAG) encoding an alanine residue at position 266 of SEQ ID NO:2. The resulting NTB-A polypeptide thus comprises 332 amino acids.

Polypeptide fragments may comprise epitopes, particularly B or T cells epitopes, functional domains or parts of human NTB-A, including portions of the polypeptide involved in an interaction with other proteins or molecules within the cell, phosphorylation domains, etc. A polypeptide fragment of this invention generally comprises less than 300 amino acids, even preferably less than 250 amino acids.

A particular polypeptide of this invention is a polypeptide comprising amino acid residues 22 to 331 of SEQ ID NO:2 or a variant thereof having an extra alanine residue at position 266. Residues 22–331 correspond to a mature NTB-A polypeptide.

An other polypeptide of this invention is a polypeptide comprising the signal peptide region of NTB-A, particularly amino acid residues 1 to 21 of SEQ ID NO:2.

An other polypeptide of this invention is a polypeptide comprising the extra-cellular region of NTB-A, particularly amino acid residues 22 to 226 of SEQ ID NO:2, or a fragment thereof comprising at least 5 contiguous amino acids. More preferred fragments comprise typically between 5 and 50 consecutive amino acids, even more preferably between 6 and 40. This region is responsible for the interaction of NTB-A with putative ligands on target cells and is particularly useful to regulate the activity of NTB-A or to screen for ligands (including the endogenous ligands) or modulators of NTB-A activity. Sub-fragments thereof can be used as well.

An other polypeptide of this invention is a polypeptide comprising the trans-membrane region of NTB-A, particularly amino acid residues 227 to 248 of SEQ ID NO:2, or a fragment thereof comprising at least 5 contiguous amino acids. More preferred fragments comprise typically between 5 and 20 consecutive amino acids, even more preferably between 6 and 15.

An other polypeptide of this invention is a polypeptide comprising the intra-cytoplasmic region of NTB-A, particularly amino acid residues 249 to 331 of SEQ ID NO:2 or a variant thereof having an extra alanine at position 266, or a fragment thereof comprising at least 5 contiguous amino acids. More preferred fragments comprise typically between 5 and 50 consecutive amino acids, even more preferably between 6 and 40. This region is responsible for the interaction of NTB-A with putative signaling molecules or receptors with NK, B or T cells and is useful to regulate the activity of NTB-A or to screen for binding partners or modulators of NTB-A activity. Sub-fragments thereof can be used as well. In this regard, a further polypeptide of this invention is a polypeptide comprising functional portions of NTB-A, such as the SH2D1A binding domain or tyrosine residues, particularly amino acid residues 271–276 (LEYVSV), 282–287 (TVYASV) or 306–311 (TIYSTI) of SEQ ID NO:2, or larger polypeptide fragments of NTB-A comprising said residues.

The invention generally relates to any polypeptides comprising an amino acid sequence encoded by a nucleic acid molecule as defined above.

The invention also includes a soluble NTB-A polypeptide.

The polypeptides of this invention may be attached to any heterologous sequence or moiety, such as stabilizing agent, a marker, a tag, a targeting moiety, a drug, a cytokine, a toxin, etc. They may also be attached or immobilized to solid supports, such as columns, beads, etc. The polypeptides of this invention are preferably in isolated or purified form (i.e., not in their natural environment) or expressed from recombinant host cells. They may be combined to other active molecules or adjuvants or solvents. The polypeptides can be used to produce antibodies, modulate an immune response, regulate the activity of NTB-A in vitro, ex vivo or in vivo, screen for compounds that modulate NTB-A activity, etc.

Host Cells

The present invention also relates to host cells comprising a nucleic acid molecule or a vector as defined above. In a preferred embodiment, the host cell comprises a nucleic acid molecule or a vector as defined above and expresses a polypeptide as defined above. The polypeptide is preferably expressed at the surface of said cell. The polypeptide may also be expressed within the cell cytoplasm or released from the cells by any means. The polypeptide may, in particular, be expressed as a soluble or secreted molecule, by removing portions thereof (e.g., the TM and/or cytoplasmic domains).

The recombinant cell can be any cultivable cell, such as prokaryotic or eukaryotic cells, including bacteria, yeasts, insect cells, plant cells, mammalian cells, etc. The cell may be a cell line or a primary culture. Typical examples include *E. coli, Saccharomyces, Kluyveromyces,* insect cells, mammalian fibroblasts or embryonic cells, HEK, CHO, COS, 3T3, 293, etc. It should be understood that the invention shall not be limited to any specific type of host cell.

In a preferred embodiment, the host cell is a cell that does not naturally express a human NTB-A polypeptide. Such host cell can be used advantageously in screening assays, with increased selectivity.

An other object of this invention is a method of preparing cells expressing a NTB-A polypeptide, said method comprising introducing into cells in vitro a nucleic acid molecule or a vector as defined above and selecting the cells or their progeny which express the polypeptide. Introduction of the nucleic acid or vector may be accomplished by various known means, such as by direct DNA transfer, lipid-mediated transfection, calcium-phosphate precipitation, electroporation, etc. The cells may be cultured in any suitable media and stored under any conventional methods.

Antibodies

The present invention also relates to an antibody that binds to a polypeptide as defined above. The antibody is preferably an antibody obtained by immunizing an animal with a polypeptide as defined above or with a host cell as defined above. In this regard, an object of this invention also includes a method of preparing an antibody, said method comprising injecting to a non-human mammal a polypeptide as defined above and collecting the antibody, serum or antibody-producing cells in said mammal.

The antibody may be a polyclonal or a monoclonal antibody as well as fragments and derivatives thereof, in particular fragments and derivatives of said antibodies having substantially the same antigenic specificity. These include antibody fragments (e.g., Fab, Fab'2, CDRs, etc), humanized antibodies, polyclonal antibodies, Single Chain antibodies (ScFv), etc. These may be produced according to conventional methods, including immunization of an animal and collection of serum (polyclonal) or spleen cells (to produce hybridomas by fusion with appropriate cell lines).

Methods of producing monoclonal antibodies from various species including mice, rodents, primates, horses, pigs, rabbits, poultry, etc. may be found, for instance, in Harlow et al (Antibodies: A laboratory Manual, CSH Press, 1988) or in Kohler et al (Nature 256 (1975) 495). Briefly, these methods comprise immunizing an animal with the antigen, followed by a recovery of spleen cells which are then fused with immortalized cells, such as myeloma cells. The resulting hybridomas produce the monoclonal antibodies and can be selected by limit dilutions to isolate individual clones.

Antibodies may also be produced by selection of combinatorial libraries of immunoglobulins, as disclosed for instance in Ward et al (Nature 341 (1989) 544).

Methods of producing polyclonal antibodies from various species, as listed above, may be found, for instance, in Vaitukaitis et al., 1971. Briefly, the antigen is combined with an adjuvant (e.g., Freund's adjuvant) and administered to an animal, typically by sub-cutaneous injection. Blood samples are collected and immunoglobulins or serum are separated.

Fab or F(ab')2 fragments may be produced by protease digestion, according to conventional techniques. Humanized antibodies can be prepared as described previously (Jones 1986).

Preferred antibodies of this invention are prepared by immunization with a NTB-A polypeptide as described above, preferably with a polypeptide of SEQ ID NO:2 or a variant having an extra alanine residue at position 266, or a fragment thereof, particularly a fragment comprising all or part of the extra-cellular domain of NTB-A. In this regard, particularly preferred antibodies of this invention are (monoclonal) antibodies that specifically bind an epitope comprised in amino acid residues 22–226 of SEQ ID NO: 2.

Most preferred antibodies of this invention are functional antibodies, i.e., antibodies that regulate the activity of NTB-A, more particularly antibodies that can activate or block the interaction of NTB-A with a target cell. Such antibodies can be further selected by contacting an antibody as disclosed above with a NK cell and a target cell, and by determining the ability of said antibody to block or to activate NK-mediated target cell lysis. The present invention shows that such functional (e.g., blocking) antibodies can be produced and used to regulate the activity of immune cells.

The antibodies may be coupled to heterologous moieties, such as toxins, labels, drugs or other therapeutic agents, covalently or not, either directly or through the use of coupling agents or linkers. Labels include radiolabels, enzymes, fluorescent labels, magnetic particles and the like. Toxins include diphtheria toxins, botulinum toxin, etc. Drugs or therapeutic agents include lymphokines, antibiotics, antisense, growth factors, etc. Methods of using such heterologous moieties are illustrated, for instance, in U.S. Pat. Nos. 4,277,149 and 3,996,345.

The antibodies of this invention have various applications, including therapeutic and diagnostic uses, and they may be used as well for immuno-purification or detection of a NTB-A polypeptide in a sample (e.g., plasma or serum samples), for instance. In particular, they can be used in vitro in screening assays as will be described below, or to detect or quantify the presence (or amounts) of NTB-A polypeptide in a sample collected from a subject, typically a blood sample from a mammalian, specifically a human subject.

Screening

The present invention provides a novel molecule involved in the activity of NK cells and potentially of T and B lymphocytes, and in the regulation of the immune system. This molecule, as well as the corresponding nucleic acids, host cells, plasmids, and binding partners thereof, can be used to screen for compounds, particularly biologically active compounds, especially in the area of immune regulation and NK regulation.

In particular, the invention also relates to methods of screening compounds comprising determining the ability of a test compound to regulate the activity of NTB-A. Within the context of the present invention, the term "activity of NTB-A" includes the expression of NTB-A as well as the biological activity of a NTB-A polypeptide. Regulating the activity of NTB-A thus includes the regulation of NTB-A synthesis (e.g., transcription, translation, trafficking, export to the cell membrane, post-translational modification, etc.)

as well as the regulation of the biological activity of NTB-A (e.g., its interaction with a ligand, the cross linking or internalisation of NTB-A, the phosphorylation or translocation of NTB-A, the association of NTB-A with an other cellular partner, etc.).

Preferred compounds are those that selectively regulate the activity of NTB-A, i.e., that essentially do not directly interfere with an other NK cell receptor, although secondary effects may be induced.

In a particular embodiment, the method comprises determining the ability of a test compound to:
bind to NTB-A,
activate NTB-A
inhibit NTB-A
inhibit NTB-A synthesis
stimulate NTB-A synthesis
modulate NTB-A binding to its putative endogenous ligand,
modulate (e.g., block or activate) the interaction of NTB-A (or cells expressing NTB-A such as NK cells, T lymphocytes, B lymphocytes, recombinant cells, etc) with target cells,
modulate (e.g., block or activate) the NTB-A-mediated NK cell induced target cell lysis,
modulate the interaction of NTB-A with SH2D1A or
modulate the interaction of NTB-A with SHP In a particular embodiment, this invention lies in a method of selecting, screening or characterizing a compound, said method comprising contacting a test compound with a polypeptide as defined above and determining the ability of said test compound to bind to said polypeptide. The polypeptide may be isolated or expressed by a cell, particularly at the surface of said cell.

The invention thus also relates to a method of selecting, screening or characterizing a compound, said method comprising contacting a test compound with a host cell as defined above (said host cell expressing a NTB-A polypeptide) and determining the ability of said test compound to bind to said polypeptide.

The ability of a test compound to bind to a NTB-A polypeptide may be determined by various techniques known in the art. In vitro, the binding may be determined by electrophoresis, SPA, FRET, etc. or by competition with a labelled ligand of a NTB-A polypeptide. In this regard, in a preferred embodiment binding is determined by measuring the ability of the test compound to modulate the binding of a labelled ligand. The labelled ligand may be, for instance, an antibody.

The invention also relates to a method of selecting, screening or characterizing a compound, said method comprising contacting a test compound with a host cell as defined above (said host cell expressing a NTB-A polypeptide) and determining the ability of said test compound to induce a biological response characteristic of a NTB-A polypeptide. The biological response may be, for instance, an association with binding partners, a cytolytic activity, etc.

In a particular embodiment, the invention comprises contacting a test compound with a NK cell in the presence of an antibody specific for NTB-A and determining the activity said test compound by measuring the cytolytic activity of said NK cells.

In a further embodiment, the invention relates to a method of selecting, screening or characterizing a compound comprising contacting a test compound with a NTB-A polypeptide in the presence of a binding partner thereof and assessing the capacity of said test compound to modulate the interaction between said NTB-A polypeptide and said binding partner. The binding partner is, for instance, all or part of SH2D1A or of SHP. The invention indeed shows that NTB-A comprises, within the intra-cytoplasmic domain, regions allowing binding to signalling molecules such as SH2D1A or of SHP. The invention further shows that such an interaction indeed occurs in physiological conditions. The screening of compounds having the ability to interfere with said interaction thus provides molecules having the ability to regulate the activity of NTB-A. Such a screening can be performed in vitro, by contacting a NTB-A polypeptide (or a portion thereof comprising all or part of the intra-cytoplasmic domain thereof) with the test compound and the binding partner.

In an other embodiment, the binding partner is a ligand of NTB-A, particularly a ligand expressed by target cells. The screening of compounds having the ability to interfere with said interaction thus provides molecules having the ability to block or stimulate NK cell-mediated target cell lysis. Such a screening can be performed in vitro, by contacting a NTB-A polypeptide (or a portion thereof comprising all or part of the extra-cytoplasmic domain thereof) with the test compound and the ligand or a target cell expressing the ligand.

In a particular embodiment, a screening method comprises (i) determining the ability of a test compound to bind to a NTB-A polypeptide and (ii) determining the ability of a test compound selected in (i) to regulate (e.g., block, reduce or stimulate) NK cell-mediated target cell lysis.

The test compound may be any synthetic compound, including organic products, lipids, peptides, proteins, nucleic acids (e.g., antisense), etc. The assay may be performed in any suitable device, such as plates, tubes, dishes, flasks, etc. Typically, the assay is performed in multi-wells plates. Several test compounds can be assayed in parallel. Furthermore, the test compound may be of various origin, nature and composition. It may be any organic or inorganic substance, isolated or in mixture with other substances. The compounds may be all or part of a combinatorial library of products, for instance.

Uses

The invention discloses a novel protein and corresponding screening methods. The protein is involved in the regulation of immune function and its modulation or regulation can thus produce a regulation of an immune function in vivo. In particular, compounds that regulate the activity of NTB-A may be used to regulate the activity of NK cells, B cells or T cells, particularly to stimulate or inhibit the activity of NK cells, more specifically the NK cells-mediated cytolysis. Such compounds are thus suitable for use in the treatment, prevention or diagnosis of pathologies in which the activity of NK cells is involved, such as viral infections, tumor or other proliferative diseases, autoimmune diseases, etc. The invention can be used, by way of example, to treat patients with X-linked lymphoproliferative disease.

An object of this invention thus lies in a method of regulating an immune response in a subject comprising administering to the subject a compound that (selectively) regulates the activity of NTB-A. The invention also relates to the use of a compound that (selectively) regulates the activity of NTB-A in the manufacture of a medicament for regulating an immune response in a subject.

The invention also relates to a pharmaceutical composition comprising a compound that regulates the activity of NTB-A and a pharmaceutically acceptable vehicle or carrier.

Particular compositions comprises a compound that stimulates the activity of NTB-A or that inhibits the activity of NTB-A.

The compositions of this invention may further comprise a compound that regulates an other NK cell receptor, particularly the 2B4 receptor. Such compositions indeed provide significant effect in vivo, particularly in XLP disease, by restoring NK or T cell activity in such patients. A particular object of this invention thus resides in a composition that comprises a compound that regulates a NTB-A receptor and a compound that regulates a 2B4 receptor, for combined, sequential or separated use. The compound is preferably a compound that inhibits or reduces NTB-A activity, particularly an antibody or a molecule selected or identified by a method as described above. The examples provided below illustrate the efficacy of such a combined treatment to restore NK cell activity in a patient with XLP disease.

The compounds may be administered according to various routes, such as by intravenous, intra-arterial, intra-muscular, intra-dermic, intra-peritoneal, etc. The compounds may be used in various dosages that can be adapted by the skilled person.

The compounds are particularly suited to stimulate an immune response in a human subject, particularly to stimulate NK cells in a human subject.

The invention also relates to methods of diagnosing a dysfunction in a subject, comprising determining the presence of a mutation or alteration in a NTB-A gene or RNA, or determining the presence or amount of a NTB-A polypeptide. These methods may be performed using antibodies or nucleic acid primers or probes as described above. The method can be performed with any sample derived from a subject, such as serum, blood, plasma, other biological fluids, tissue samples, etc.

Further aspects and advantages of the present invention will be disclosed in the following examples, which should be regarded as illustrative and not limiting the scope of this applications. All cited references are incorporated therein by reference.

LEGEND TO THE FIGURES

FIG. 1. Biochemical characterization of NTB-A molecules. NK cell, TCR gamma delta cell and thymocyte (Thy) populations that had been surface labeled analysis of NTB-A molecules in redirected killing assay and in NK-mediated killing of EBV target cells. (a) Representative NKp46 bright (MX367, CC16) and NKp46 dull (HER12, HER3) NK cell clones were analyzed in a redirected killing assay against (FcR) P815 murine target cells either in the absence or in the presence of mAbs specific for the indicated molecules. All the mAbs were of the IgG1 subclass. (b) The representative NKp46 bright clone (MOA110) either untreated or modulated with anti-NKp46 (KL247, IgM) mAb was tested for cytolytic activity in a redirected killing assay against murine P815 target cells either in the absence or in the presence of mAbs specific for the indicated molecules. In both experiments the E/T ratio used was 8:1. (c) Two representative NKp46 bright NK cell clones (MX367 and MOA110) were analyzed for cytolytic activity against the LCL 721.221 EBV cell line (HLA class I CD48 FcR) either in the absence or in the presence of mAbs specific for the indicated molecules. The E/T ratio used was 2:1. (d) The NK92 NK cell line was analyzed for cytolytic activity against the (FcR) P815 murine target cells or the LCL 721.221 EBV cell line, either in the absence or in the presence of mAbs specific for the indicated molecules. The E/T ratio used was 5:1. The results are representative of seven independent experiments. The standard deviation of the mean of the triplicates was 4%.

FIG. 2. Functional analysis of NTB-A molecules in redirected killing assay and in NK-mediated killing of EBV+ target cells. (a) Representative NKp46 bright (MX367, CC16) and NKp46 dull (HER12, HER3) NK cell clones were analyzed in a redirected killing assay against (FcγR+) P815 murine target cells either in the absence or in the presence of mAbs specific for the indicated molecules. All the mAbs were of the IgG1 subclass. (b) The representative NKp46 bright clone (MOA110) either untreated or modulated with anti-NKp46 (KL247, IgM) mAb was tested for cytolytic activity in a redirected killing assay against murine P815 target cells either in the absence or in the presence of mAbs specific for the indicated molecules. In both experiments the E/T ratio used was 8:1. (c) Two representative NKp46 bright NK cell clones (Mx367 and MOA110) were analyzed for cytolytic activity against the LCL 721.221 EBV cell line (HLA class I- CD48+, FcγR−) either in the absence or in the presence of mAbs specific for the indicated molecules. The E/T ratio used was 2:1. (d) The NK92 NK cell line was analyzed for cytolytic activity against the (FcgR+) P815 murine target cells or the LCL 721.221 EBV cell line, either in the absence or in the presence of mAbs specific for the indicated molecules. The E/T ratio used was 5:1. The results are representative of seven independent experiments. The standard deviation of the mean of the triplicates was <4%.

FIG. 3. Analysis of the NTB-A-specific signal transduction pathway. (a) Cell lysates derived from a polyclonal NK cell population either untreated (−) or treated (+) with sodium pervanadate (100 M, 10 min, 37 C), were sequentially immunoprecipitated (IP) with anti-2B4 and anti-NTBA mAbs. Samples were analyzed under reducing conditions in 8% SDS-PAGE and probed with anti-phosphotyrosine (anti-P-Tyr). (b) Cell lysates derived as in panel a were sequentially immunoprecipitated with anti-2B4, anti-NTB-A, anti-NKp46, and anti-IRp60. Equal amounts of each immunoprecipitate were analyzed under reducing conditions in 8% SDS-PAGE and probed with either anti-SHP-1 or anti-SHP-2 mAbs. (c) Cell lysates derived as in panel a were sequentially immunoprecipitated with anti-2B4, anti-NTB-A, and anti-SH2D1A. Samples were analyzed under reducing conditions in 14% SDS-PAGE and probed with anti-SH2D1A antiserum. In each panel molecular weight markers (kD) are indicated.

FIG. 4. Functional analysis of NTB-A molecules in NK cells derived from XLP patients. (a) Polyclonal NK cell population derived from XLP patient A was analyzed for cytolytic activity in a redirected killing assay against the (FcgR+) P815 target cell line either in the absence or in the presence of mAbs specific for the indicated molecules. The E/T ratio used was 8:1. All the mAbs used in this experiment were of the IgG1 isotype. (b) Polyclonal NK cell populations derived from XLP patient A or from a healthy donor were analyzed for cytolytic activity against the LCL 721.221 EBV cell line (HLA class I CD48 FcgR+) either in the absence or in the presence of mAbs specific for the indicated molecules. The E/T ratio used was 6:1. The results are representative of six independent experiments. The standard deviation of the mean of the triplicates was 5%.

FIG. 5. Surface expression of NTB-A in COS-7 cells transfected with the VR1012/KALI construct. COS-7 cells transfected with VR1012/KALI construct were stained with MA127 (anti-NTB-A) or PP35 (anti-2B4) mAbs followed by PE-conjugated goat anti-mouse second reagent and analyzed by flow cytometry. White profiles indicate cells incubated with the second reagent only.

FIG. 6. (A) Amino acid sequence of NTB-A molecule (SEQ ID NO:2). The putative signal peptide is indicated in lower case letters (residues 1–21) and the trans-membrane region is boxed. Tyrosine-based motifs present in the cytoplasmic tail are underlined. (B) Nucleic acid and amino acid sequence of NTB-A molecule (SEQ ID NO:1).

BRIEF DESCRIPTION OF THE SEQUENCES

SEQ ID NO: 1 is a nucleic acid and amino acid sequences of the NTB-A molecule.
SEQ ID NO: 2 is an amino acid sequence of the NTB-A molecule.
SEQ ID NO: 3 is a primer KALI-up sequence.
SEQ ID NO: 4 is a primer KALI-down sequence.

Materials and Methods

Monoclonal Antibodies (mAbs)

MA127 mAb was obtained by immunizing a 5-wk-old-BALB/c mouse with the NK clone KK4 (surface phenotype: CD3 CD16 CD56 NCR CD94/NKG2A) as described previously (6, 8, 9). The following mAbs, produced in our lab, were used in this study: JT3A (IgG2a, anti-CD3), BAB281 and KL247(IgG1 and IgM, respectively, anti-NKp46), Z231 and KS38(IgG1 and IgM, respectively, anti-NKp44), Z25 and F252 (IgG1 and IgM, respectively, anti-NKp30), PP35 and S39 (IgG1 and IgG2a, respectively, anti-2B4), KD1 and c127 (IgG2a and IgG1, respectively, anti-CD16), c218 and GPR165 (IgG1 and IgG2a, respectively, anti-CD56), A6-136 (IgM, anti-HLA class I), XA185 (IgG1, anti-CD94), and Z199 and Z270 (IgG2b and IgG1, respectively, anti-NKG2A). D1.12 (IgG2a, anti-HLA-DR) mAb was provided by Dr. R. S. Accolla (Pavia, Italy). HP2.6 (IgG2a, anti-CD4) mAb was provided by Dr. P. Sanchez-Madrid (Madrid, Spain). WT31 (IgG1, anti-TCR-/) was purchased by Becton Dickinson.

Purification of Polyclonal or Clonal NK Cell Populations

To obtain PBLs, PBMCs were isolated on Ficoll-Hipaque gradients and depleted of plastic-adherent cells (6). Enriched NK cells were isolated by incubating PBLs with anti-CD3 (JT3A), anti-CD4 (HP2.6), and anti-HLA-DR (D1.12) mAbs (30 min at 4C) followed by goat anti-mouse coated Dynabeads (Dynal; 30 min at 4 C) and immunomagnetic depletion (6). CD3 CD4 DR cells were cultured on irradiated feeder cells in the presence of 100 U/ml rIL-2 (Proleukin; Chiron Corp.) and 1.5 ng/ml PHA (GIBCO BRL) in order to obtain polyclonal NK cell populations or, after limiting dilution (6, 8), NK cell clones.

XLP Patients

The XLP patients analysed in this study are affected by mutations at the SH2D1A locus represented by: G to T nucleotide change at the translation initiation codon (ATG to ATT), leading to a motioning to isoleucine amino acid change (patient A) and C to T nucleotide change at position 163, leading to premature termination at codon 55 (patients B and C). As described previously (28), these mutations result in a complete absence of SH2D1A protein.

Cytolitic Activity and Flow Cytofluorimetric Analysis

NK cells were tested for cytolytic activity against the (FcR) P815 murine mastocytoma cell line or the lymphoblastoid cell line (LCL) 721.221 EBV cell line (HLA class I CD48 FcR) in a 4-h 51 Cr-release assay as described previously (6, 8, 9, 28). The concentrations of the various mAbs added were 0.5 g/ml for redirected killing or 10 g/ml for masking experiments. The E/T ratios are indicated in the text. For one- or two-color cytofluorimetric analysis FAC-SCAN; Becton Dickinson) cells were stained with the appropriate mAbs followed by PE- or FITC-conjugated isotype-specific goat anti-mouse second reagent (Southern Biotechnology Associates, Inc. [6, 8, 9]).

Biochemical Characterization of NTB-A Molecules

Cells were labeled with Biotin (Pierce Chemical Co.) as described previously (28). 1% NP-40 cells lysates were immunoprecipitated with Sepharose-PA (Amersham Pharmacia Biotech)-coupled mAbs. Samples were analyzed by discontinuous SDS-PAGE either undigested or digested with N-glycosidase F (Boebringer; reference 28) and transferred to Immobilon P (Millipore). After staining with Neutravidin (Pierce Chemical Co.), the Renaissance Chemiluminescence Kit (NEN Life Science Products) was used for detection.

Analysis of the NTB-A Signal Transduction Pathway

NK cells ($10^8$) were stimulated or not with 100 M sodium pervanadate (28). 1% NP-40 or 1% digitonin cell lysates were immunoprecipitated with Sepharose-PA (Amersham Pharmacia Biotech)-coupled mAbs. Samples were analyzed in discontinuous SDS-PAGE, transferred to Immobilon P (Millipore), and probed with: (a) anti-phosphotyrosine mAb (PY20-HRPO; Transduction Laboratories); (b) anti-SHP-2 or anti-SHP-1 mAbs (PTP1D and PTP1C, respectively; Transduction Laboratories) followed by rabbit anti-mouse-HRPO (Dako); (c) anti-SH2D1A rabbit anti-serum (produced by Eurogentec S.A; reference 28) followed by donkey anti-rabbit-HRPO (Amersham Pharmacia Biotech). The Renaissance Chemiluminescence Kit (NEN Life Science Products) was used for detection. Putative NTB-A association with known signal transducing molecules was analyzed by probing NTB-A immunoprecipitates, obtained from 1% digitonin cell lysates, with anti-FcRI (provided by E. Vivier, Marseille, France), anti-DAP12 (SI-28; reference 10), and anti-LAT (UBI; Upstate Biotechnology) antisera or with anti-CD3 mAb (TIA/2; Immunotech).

Library Screening by cDNA Expression in COS-7 and Sib Selection.

The library screening was performed as described previously (7). In brief, the cDNA library, fractionated in 10 different pools, was transiently transfected in COS-7 cells using non liposomal FuGene-6 reagent (Roche) following the manufacturer's instruction. Selection of positive pools was performed by immuno-cytochemical staining using the specific anti-NTB-A mAb MA127 and sib selection.

DNA Sequencing and Reverse Transcription PCR Analysis.

DNA sequencing was performed using d-Rhodamine Terminator Cycle Sequencing kit and a 377 ABI automatic sequencer (PerkinElmer/Applied Biosystems). The analysis of the putative protein coded by the KALI cDNA was performed using the GeneWorks 2.5.1N and the site see Worldwide Website: genome.cbs.dtu.dk/htbin/nph-webface. RNA, extracted using RNAzoP (Cinna/Biotecx), and oligo (dT)-primed cDNA were prepared from polyclonal NK cell populations and thymocytes by standard techniques. The set of primers KALI-up (containing the ATG initiation codon): 5'GCG GAA AGC ATG TTG TGG (SEQ ID NO: 3) and KALI-down (de-signed in the 3 untranslated region): 5'TCA TTC CCG AAT TCC TCT G (SEQ ID NO: 4) were used to amplify the KALI-ORF. 30 cycles PCR (30 s, 95° C.; 30 s, 60° C.; and 30 s, 72° C.) was performed using TAQ-GOLD (PerkinElmer/Applied Biosystems) after preactivation of 12 min at 95° C. The obtained amplification products were cloned into pcDNA3.1/V5/His-TOPO (topoisomerase) vector using the Eukaryotic-TOPO-TA (topoisomerase) Cloning kit (Invitrogen) and sequenced.

Transient Transfection

COS-7 cells ($5.10^5$/plate) were transfected with VR1012/KALI construct using FuGene-6 reagent (Roche; reference 23). After 48 h, transfected cells were stained with MA127 (anti-NTB-A) and PP35 (anti-2B4; as negative control) mAbs followed by Ig-G1 PE-conjugated goat anti-mouse second reagent and analyzed by flow cytometry using a FACSORT (Becton Dickinson).

Chromosomal Localization and Zoo-Blot Analysis

The Somatic Cell Hybrid blot (BIOS Laboratories), containing 20 multichromosomal somatic human/hamster cell hybrids plus 3 control genomic DNAs (human, hamster, and mouse) was used to assign the KALI gene to a specific chromosome (10). The open reading frame of KALI gene was used as probe to perform high stringency hybridization (37). Analysis of cross-specific conservation of KALI gene was performed using Zoo-Blot from CLONTECH Laboratories, Inc. This Southern blot contained genomic DNA from human, Rhesus monkey, Sprague-Dawley rat, BALB/c mouse, dog, cow, rabbit, chicken, and *Saccharomyces cerevisiae* yeast. Washes were carried out under low stringency condition (7).

Results

Identification and Cellular Distribution of NTB-A Molecule.

Mice were immunized with the human NK cell clone KK4 (surface phenotype: CD3 CD16 CD56 NCR CD94/NKG2A). After cell fusion, a mAb, termed MA127 (IgG1), was selected on the basis of its ability to induce cytotoxicity in polyclonal or clonal NK cells (including the immunizing NK cell clone KK4) in a redirected killing assay against the FcR P815 murine target cells (see below). The cell surface distribution of the MA127-reactive molecules was analyzed by indirect immunofluorescence and cytofluorimetric analysis in peripheral blood mononuclear cells (PBMCs) from normal donors. As shown in Table 1, MA127 mAb brightly stained NK, T, and B lymphocytes. On the other hand, no reactivity was detected with monocytes, granulocytes, and a panel of nonlymphoid cell lines. Polyclonal populations of either NK cells or TCR-/ cells or thymocytes were surface-labeled with biotin and cell lysates were immunoprecipitated with MA127 mAb. In all instances, this mAb immunoprecipitated a surface molecule of 60 kD both under reducing (FIG. 1) and nonreducing conditions (not shown). The protein back-bone remaining after treatment with N-glycosidase F, displayed a molecular mass of 37 kD. These data suggested that MA127 mAb may recognize a novel triggering molecule expressed not only by NK cells but also by T and B lymphocytes; this molecule was thereafter termed NK-T-B-antigen (NTB-A).

Clonal Heterogeneity in Response to Anti-NTB-A mAb-mediated Cross-linking.

Figure 2A:
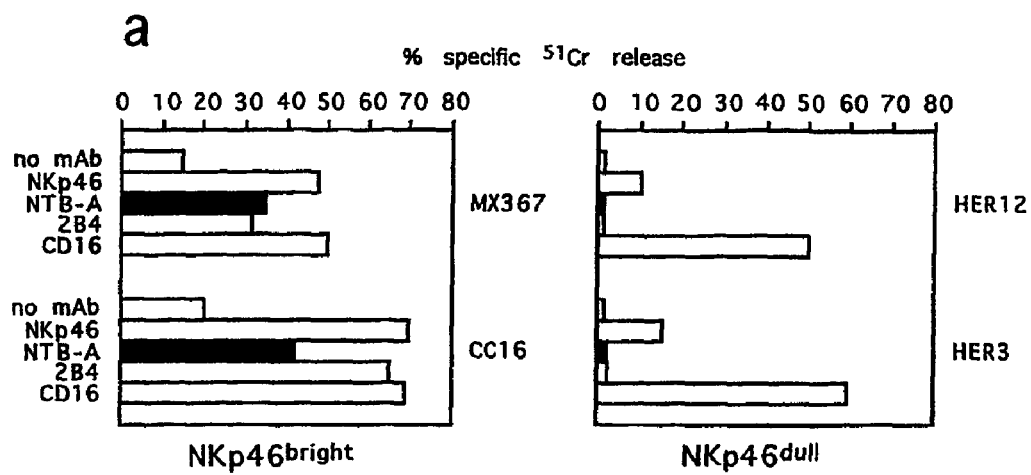
Figure 2B:
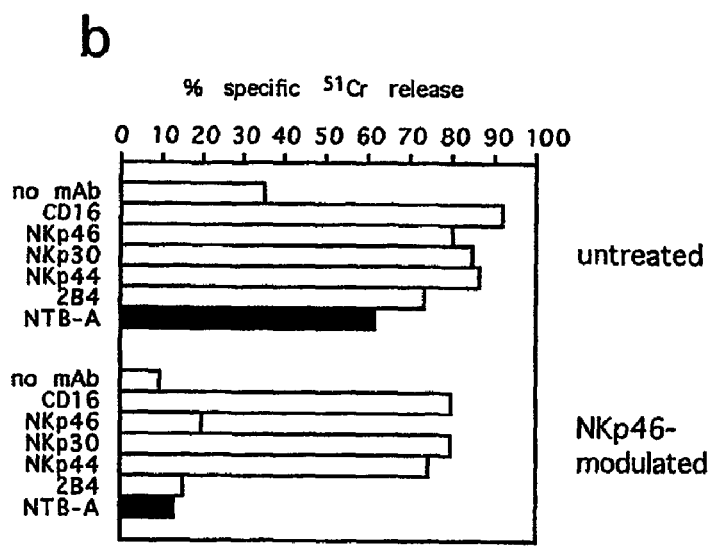
Figure 2C:
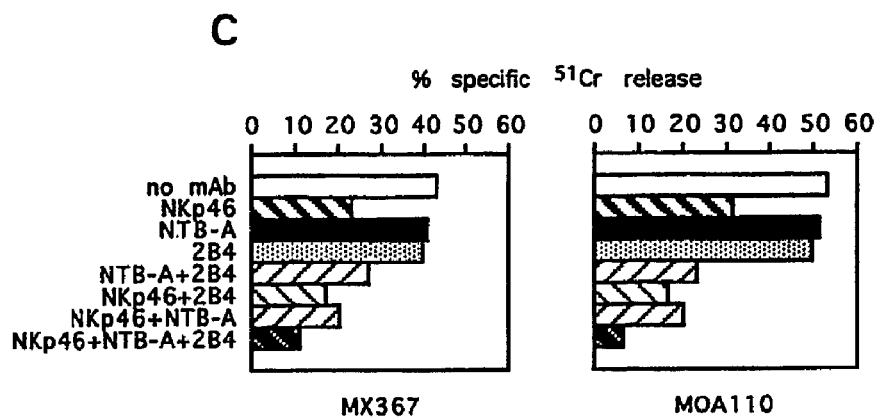

It has been shown that heterogeneity exists among NK cell clones in their ability to kill a given HLA class I-negative target cell and that this reflects the differential expression of NCRs (12). Thus, NK cell clones displaying strong cytolytic activity express high levels of NCRs (NCR bright) whereas those with low cytolytic activity express low amounts of NCRs (NCR dull). Importantly, the NCR surface density was also found to correlate with the function of 2B4. Thus, although 2B4 is expressed at similar surface densities in both types of NK cell clones, it induces cytotoxicity only by the NCR bright ones (23). A panel of NK cell clones displaying either NCR bright or NCR dull phenotype was analyzed in a redirected killing assay against P815 target cells in the presence of MA127 mAb. As shown in FIG. 2a, whereas NKp46 bright clones were responsive both to anti-NCR and anti-2B4 or anti- NTB-A mAbs, NKp46 dull clones responded poorly to all of these mAbs (although they did respond efficiently to anti-CD16 mAb). Remarkably, all the NK cell clones analyzed expressed similar surface densities of NTB-A (not shown). To further explore the relationship between responsiveness to anti-NTB-A mAb and surface density of NKp46, we analyzed the effect of surface modulation of NKp46 molecules. To this end, NKp46 bright clones were incubated overnight in the presence of immobilized anti-NKp46 mAb (KL247, IgM). This resulted in a virtually complete disappearance of NKp46 molecules from the cell surface (23; data not shown). This treatment did not affect the surface expression of NTB-A or of other NK cell surface molecules. NKp46-modulated clones were used as effectors in a redirected killing assay against P815 target cells in order to analyze their responsiveness to mAbs directed to different surface molecules. In agreement with previous data indicating that NKp46 functions as the major human receptor in the recognition and lysis of murine targets (7, 12, 38), NKp46-modulated NK cells displayed a sharply reduced ability to spontaneously lyse P815 cells (in the absence of mAbs; FIG. 2b; reference 23). Importantly, the analysis of the effect of different mAbs revealed that the un-responsiveness was limited not only to anti-NKp46 or anti-2B4 mAbs (23) but also to antiNTB-A mAb. On the contrary, responses to anti-NKp44, anti-NKp30, or anti-CD16 mAb were not affected (23). These data are reminiscent of previous data using anti-2B4 mAbs (23) and suggest that also NTB-A may function as a coreceptor in the mechanism of NK cell activation. Note, however, that both the cell surface distribution and the molecular mass of NTB-A are clearly distinct from those of 2B4 (see Table 1 and FIG. 1).

Involvement of NTB-A in NK-mediated Killing of EBV Target Cells.

Figure 2D:
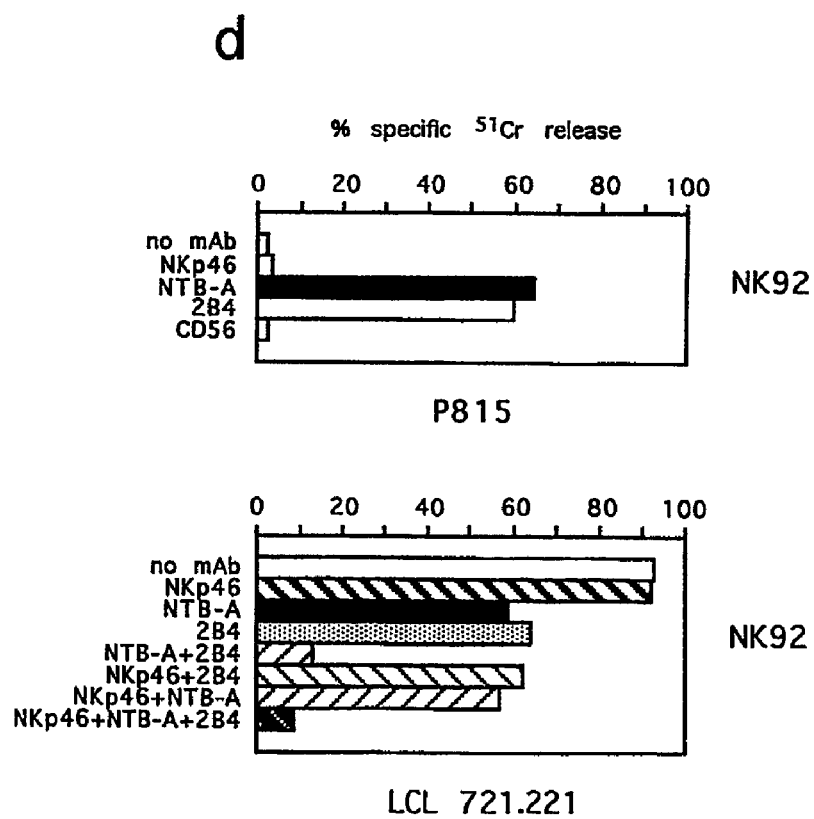

2B4 has been shown to cooperate with NKp46 in the process of recognition and killing of EBV-infected cells such as the (HLA class I CD48 FcR ) LCL 721.221 (28). On the contrary, the contribution of other triggering receptors expressed by NK cells, including NKp30, NKp44, and NKG2D, in NK-mediated lysis of LCL 721.221 is marginal or even absent (data not shown). We analyzed whether also NTB-A is involved in lysis of these target cells. Thus, NK cell clones, derived from normal donors, were assessed for cytolytic activity against the LCL 721.221 (FIG. 2c) or Daudi Burkitt lymphoma (not shown) cell lines, either in the absence or in the presence of mAbs directed to NTB-A, 2B4, or NKp46. mAb-mediated blocking of either NTB-A or 2B4 did not significantly affect the NK-mediated killing of these targets. However, the combined use of mAbs directed to NTB-A and 2B4 resulted in a partial inhibition of lysis. Inportantly, the inhibitory effect obtained by mAb-mediated masking of NKp46 was significantly incremented in the presence of either anti-NTB-A or anti-2B4 mAbs and maximal inhibition was obtained when the three molecules were simultaneously blocked by the respective mAbs. Isotype-matched anti-CD56 mAb used either alone or in combination had no inhibitory effect (not shown). These data suggest that, in normal cells, NTB-A, together with 2B4, cooperates with NKp46 in the induction of NK-mediated cytotoxicity against EBV target cells. Moreover, they suggest that NTB- A, similar to 2B4, recognizes cell surface ligand(s) expressed on EBV targets. However, it should be stressed that data obtained using normal NK cells may be of difficult interpretation because different receptors (such as NKp46) and coreceptors (such as NTB-A and 2B4) are involved in the cytolytic activity against EBV targets. On the other hand, that NTB-A, similar to 2B4 (28), is indeed capable of recognizing EBV target cells was confirmed by experiments in which the NK92 leukemic NK cell line was used as source of effector cells. This cell line is NTB-A 2B4 but expresses very low amounts of NKp46 (not shown). Accordingly, mAb-mediated cross-linking of NKp46 fails to induce NK92-mediated cytotoxicity against P815 in a redirected killing assay (FIG. 2d). Importantly however, in this assay the cytotoxicity of NK92 cells could be strongly enhanced by mAb-mediated cross-linking of either NTB-A or 2B4. These data suggest that in the case of NK92 cells (different from normal NK cells) the NTB-A and 2B4-mediated activation was mostly NKp46 independent. Thus, NK92 cell line offered a useful tool to clarify the involvement of NTB-A in the recognition and killing of EBV target cells. Indeed, as shown in FIG. 2d, NK92 cells were strongly cytolytic against LCL 721.221 target cells. mAb-mediated masking of either NTB-A or 2B4 resulted in a consistent inhibition of cytotoxicity whereas the combined use of both mAbs resulted in the virtual abrogation of NK92-mediated killing of LCL 721.221. Altogether, these data support the notion that NTB-A is involved in the recognition of EBV targets.

Analysis of the NTB-A-mediated Signal Transduction Pathway.

Figure 3A:
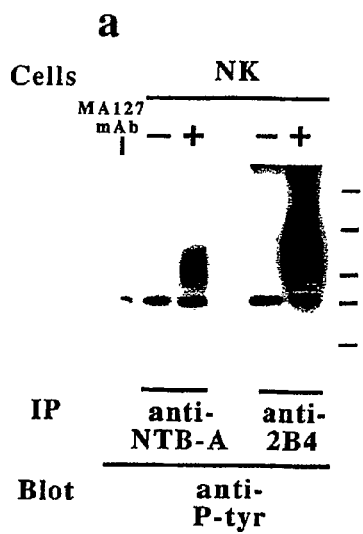
Figure 3C:
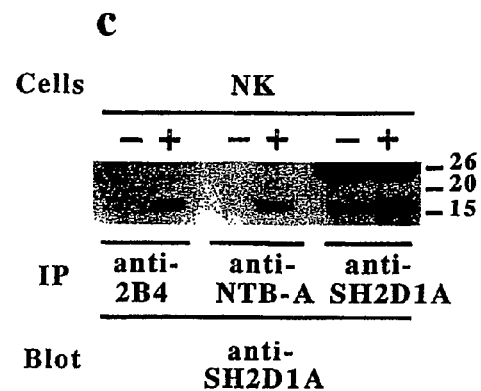
Figure 3B:
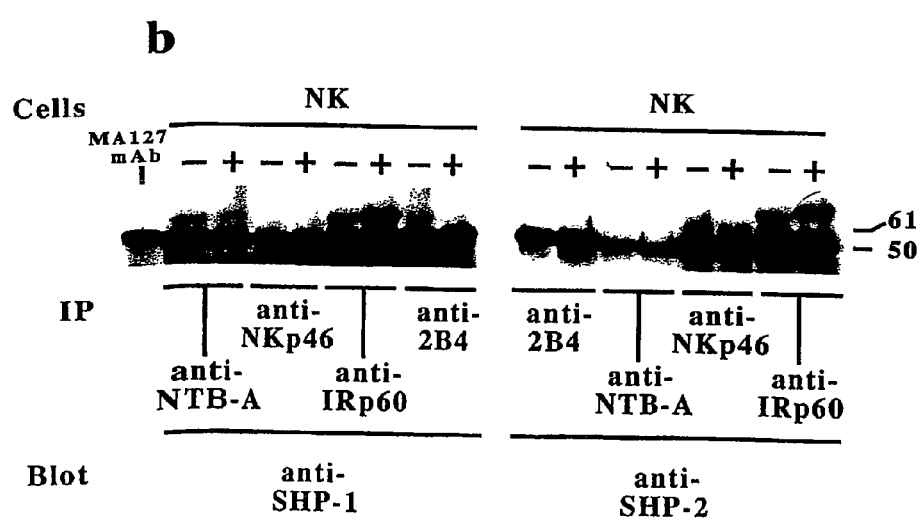

NTB-A molecules were immunoprecipitated from polyclonal NK cell populations treated or not with sodium pervanadate. Tyrosine phosphorylation of NTB-A molecules was consistently detectable in immunoprecipitates obtained from sodium pervanada-tetreated but not from untreated cells (FIG. 3a). On the contrary, NTB-A did not associate with signal transducing polypeptides, including CD3, FcRI, and DAP12 (not shown). These data suggested that, different from NCRs but similar to 2B4, NTB-A molecules may display tyrosine-based motifs in their intracytoplasmic portion. These motifs were likely to mediate the association with intracytoplasmic molecules involved in the transduction of activating signals. To analyze this possibility, NTB-A immunoprecipitates, obtained as above, were probed with anti-SH2D1A antiserum or with mAbs specific for SHP-1 or SHP-2. As a control, identical cell lysates were immunoprecipitated with mAbs specific for 2B4, or for the inhibitory receptor protein 60 (IRp60) or NKp46. 2B4 has been shown to associate with SHP-1 and, upon sodium pervanadate treatment or mAb-mediated cross-linking, with SH2D1A (27–29). On the other hand, IRp60 is an immune tyrosine-based inhibitory motif (ITIM)-bearing receptor that associates with both SHP-1 and SHP-2 (39), while NKp46, lacking tyrosine-based motifs in the cytoplasmic tail, transduces the activating signals via the association with CD3 and FcRI ITAM-containing transmembrane adaptor molecules (4). This analysis revealed the presence of SHP-1 in NTB-A immunoprecipitates obtained from both untreated and sodium pervanadate-treated cells. In contrast, the association of NTB-A with SHP-2 could be detected only in treated cells (FIG. 3b). Notably, treatment with sodium pervanadate also led to the association of NTB-A with SH2D1A molecules (FIG. 3c). Altogether, these data strengthened the idea that NTB-A molecules, although exhibiting a distinct surface distribution in PBMCs, display functional and molecular characteristics similar to 2B4.

NTB-A Mediates Inibitory Rather than Activating Signals in XLP-NK Cells.

Figure 4A:
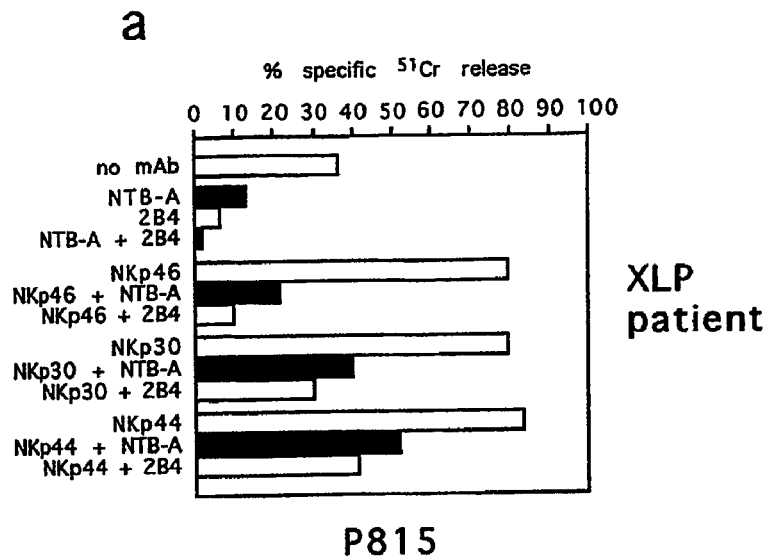
Figure 4B:
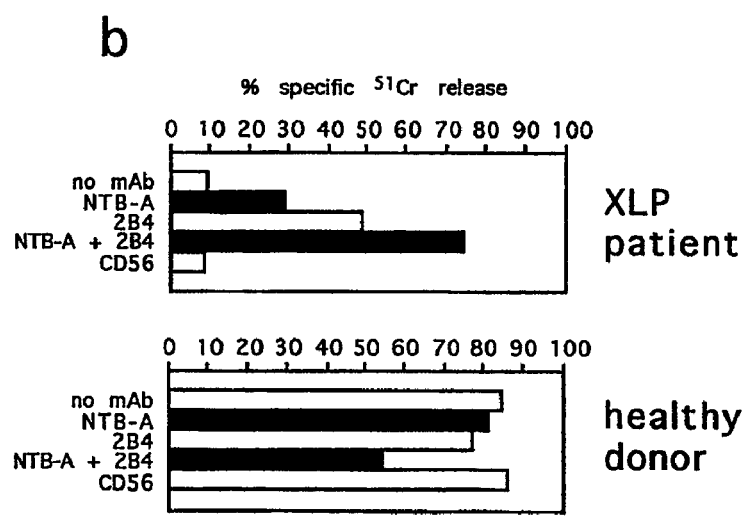

In view of the similarities with 2B4, we analyzed the function of NTB-A in polyclonal and clonal NK cells from different patients affected by XLP (see Materials and Methods). XLP-NK cells were analyzed in a redirected killing assay against P815 murine targets either in the absence or in the presence of mAbs specific for various surface molecules including NTB-A and 2B4. As shown in FIG. 4a, and in agreement with previous data (28), in NK cells from the representative XLP patient A, 2B4 exhibited inhibitory rather than activating function whereas CD16 (not shown) and NCRs displayed normal triggering capability. Importantly, cross-linking of NTB-A by specific mAb also resulted in a marked inhibition of spontaneous cytotoxicity. An even greater inhibitory effect was observed in the presence of both NTB-A- and 2B4-specific mAbs (FIG. 4a). Moreover, cross-linking of NTB-A was able to inhibit the cytolytic activity induced by anti-CD16 (not shown) or anti-NCR mAbs. Consistent with previous results (28), a similar inhibitory activity was observed in the presence of anti-2B4 mAb. Although not shown, the absence of SH2D1A in XLP-NK cells did not affect the level of expression of NTB-A at the cell surface. Based on the observation that NTB-A, similar to 2B4, may recognize cell surface ligand(s) expressed on EBV target cells (see above) we asked whether in XLP-NK cells this interaction could induce the generation of inhibitory signals via NTB-A. XLP-NK cells were further analyzed for their ability to lyse the (HLA class I FcR) LCL 721.221 EBV cell line expressing large amounts of CD48 (i.e., the natural ligand of 2B4). In agreement with previous report (28), these target cells were efficiently lysed by normal NK cells while they were resistant to lysis by XLP-NK cells (FIG. 4b). mAb-mediated masking of either 2B4 (28) or NTB-A molecules resulted in partial restoration of lysis of LCL 721.221 cells; this effect was further incremented by the simultaneous masking of both molecules (FIG. 4b). It is of note that, unlike 2B4, NTB-A molecule is expressed by both effectors (NK cells) and targets (B cells). However, restoration of lysis could be detected only upon pretreatment of effector but not of target cells with anti-NTB-A mAb (not shown). Similar results were obtained in XLP-NK cells derived from patient B (28) and patient C carrying the same mutation (not shown).

Thus, the lack of SH2D1A in XLP patients resulted in a profound dysfunction not only of 2B4 but also of the newly identified NTB-A molecule. Accordingly, both molecules appear to contribute to the inability of XLP-NK cells to kill EBV target cells.

Molecular Cloning and Characterization of the cDNA Encoding the NTB-A Surface Molecule.

The cDNA encoding NTB-A molecule was isolated from an NK cell-derived cDNA expression library using MA127 mAb (7). This cDNA (referred as KALI) was characterized by a length of 2,744 bp. Transfection of the VR1012/KALI construct in COS-7 cells allowed the surface expression of molecules that were brightly stained by MA127 mAb (FIG. 5). Moreover, MA127 mAb specifically immunoprecipitated from cell transfectants a protein that, after treatment with N-glycosidase F, displayed a protein backbone identical to that of NTB-A molecules derived from polyclonal NK cells (not shown). The predicted amino acid sequence is consistent with a type I transmembrane protein of 331 amino acids belonging to the Ig-SF (FIG. 6). The NTB-A molecule is characterized by a 21 amino acid leader peptide preceding an extracellular region of 204 residues. Protein sequence analysis suggests that the extracellular portion is composed by a N-terminal V-type domain (lacking the classical disulfide bond) followed by a C2-type domain (characterized by two possible intradomain disulfide bonds). The extracellular portion contains seven potential N-linked glycosylation sites, but no putative O-glycosylation sites. A 23 amino acid long transmembrane region, lacking charged amino acid residues, precedes a relatively long (83 amino acids) intracytoplasmic portion that contains three tyrosine residues. Two tyrosine residues are part of the TxYxxV/I motif that has recently been described in the 2B4 cytoplasmic tail (25–28). Notably, these motifs are believed to represent consensus sequence for the association with SH2D1A. The third tyrosine residue is included in a classical ITIM (I/V/L/SxYxxL/V; reference 3) that is absent in the 2B4 cytoplasmic tail. Reverse transcription (RT)-PCR performed on RiNA derived from different NK cell clones using KALI ORF-specific primers revealed the existence of a second cDNA coding for a putative allelic isoform of NTB-A. This cDNA is characterized by an extra codon (CAG) resulting in the insertion of an Ala residue at position 266 of the mature protein. Comparison of the NTB-A amino acid sequence in GenBank/EMBL/DDBJ database with other previously identified proteins revealed homology with CD84 (40) (25% of identity). Chromosomal localization by Southern blot analysis revealed segregation of NTB-A encoding gene on human chromosome 1 (not shown). Remarkably, the same chromosomal localization has been established also for all the genes coding for the various members of the CD2 subfamily (24). This finding, together with the particular core structure of the Ig-like domains (characterized by an N-terminal non-disulfide-bonded Ig-V domain and by a membrane-proximal Ig-C2 domain containing two possible intradomain disulfide bonds) suggests that NTB-A represents a novel member of the CD2 subfamily. Finally, hybridization of zooblot with KALI ORF probe suggested a cross-species conservation between human and monkey (not shown).

DISCUSSION

In this study we have identified, molecularly characterized, and cloned NTB-A, a novel triggering surface molecule belonging to the CD2 subfamily, that is expressed on resting and activated lymphoid populations including NK, T, and B lymphocytes. Similar to 2B4 (23), triggering of normal NK cells via NTB-A requires the simultaneous engagement of NKp46. The role of NTB-A as a co-receptor is further documented by mAb-mediated masking experiments. In these experiments, the lysis of EBV-infected B cell lines mediated by normal NK cells was inhibited by the simultaneous masking of NTB-A, NKp46, and 2B4. Biochemical analysis revealed that NTB-A, similar to 2B4 (27, 28), associates with SH2D1A and SHP. SH2D1A is a small intracytoplasmic adaptor molecule the expression of which appears to be highly regulated. Indeed, very low levels of SH2D1A can be detected in resting cells while they dramatically increase upon cell activation (41). It is unlikely that SH2D1A may play a direct role in co-stimulation. On the other hand, it is likely that SH2D1A simply participates to the transduction of NTB-A mediated activating signals by competing with the intracytoplasmic phosphatases for binding to this activating coreceptor. Along this line, previous reports showed that SH2D1A is crucial for the transduction of activating signals via 2B4 (27, 28) and CD150 (42).

Moreover, 2B4 tyrosine phosphorylation and association with SH2D1A was detected not only upon sodium pervanadate treatment but also upon 2B4 mAb-mediated cross-linking (29). The finding that NTB-A associates upon tyrosine phosphorylation with SH2D1A led us to investigate the function of NTB-A in individuals affected by XLP (33, 34). XLP is characterized by critical mutations in the SH2D1A encoding gene (30, 35, 36). XLP patients suffer from a severe immunodeficiency resulting in the inability to control EBV infections. Previous studies suggested that SH2D1A-associated molecules may play an important role in the failure of cytolytic cells to kill ED V-infected target cells. In this context, 2B4 molecule, which functions as a triggering coreceptor in normal NK cells (23), has been shown to display a profound alteration of the signaling pathway in the case of XLP-NK cells. Thus, due to the absence of SH2D1A association, 2B4 displays an opposite function, i.e., mediates inhibitory rather than activating signals. 2B4 engagement either by specific mAb or by its natural ligand (CD48) expressed at high density in EBV-infected cells, resulted in down regulation of XLP-NK cell-mediated cytotoxicity. This was true both for the spontaneous cytolytic activity and for the NK cell triggering induced via different activating receptors (i.e., NKp46; reference 28, and this report). Analysis of the amplified cDNA obtained by RT-PCR in polyclonal XLP-NK cells revealed, in all samples analyzed, that the NTB-A sequence is identical to that obtained from healthy donors (not shown). Moreover, cytofluorimetric analysis of XLP-NK cells showed that the absence of SH2D1A molecule does not affect the surface expression of NTB-A. Importantly, in XLP-NK cells NTB-A appears to play a role similar to 2B4 (28). Indeed, in the absence of SH2D1A, NTB-A does not transduce triggering but rather inhibitory signals. This can easily be appreciated in redirected killing assays in which mAb-mediated cross-linking of NTB-A results in inhibition of both the spontaneous and the NCR-mediated cytotoxicity of XLP-NK cells. More importantly, similar inhibitory signals were generated when XLP-NK cells interacted with EBV target cells. In addition to the 2B4/CD48 interaction (28), another inhibitory signal was generated by the interaction between NTB-A and still unknown ligand(s) expressed on EBV cells. Thus, mAb-mediated blocking of NTB-A partially restored the XLP-NK cell-mediated lysis of EBV targets while it had no effect on the lysis of different tumor targets including melanomas, lung carcinomas, T cell lymphomas, and cervical carcinomas (not shown). This suggests that, similar to CD48, the expression of NTB-A ligand(s) may be restricted to certain cell types. Alternatively, only some cells may express sufficient surface densities of the ligand(s) to allow signalling upon binding with NTB-A. It is possible that NTB-A similar to CD150 (42) may display homophilic interactions or interact with other members of the CD2 subfamily (as in the case of CD2/CD48, CD2/CD58, and 2B4/CD48 interactions) (21, 22, 43). Preliminary data would suggest that the ligand for NTB-A is not represented by CD48 (i.e., the 2B4 ligand). Thus, upon simultaneous masking of both NTB-A and 2B4, an additive effect occurs in the restoration of XLP-NK cell-mediated lysis of EBV target cells (see above). Moreover, whereas only a partial restoration of NK-mediated cytotoxicity occurred upon mAb-mediated masking of CD48 on EBV target cells, a strong increment of lysis could be detected by the simultaneous masking of NTB-A on XLP-NK cells (data not shown). In this study the analysis of the cytolytic activity of XLP-NK cells against EBV targets has been mainly evaluated against HLA class I EBV LCL in order to avoid interference due to killer inhibitory receptor (KIR)/HLA class I interactions. We previously showed, in XLP patients, that the recovery of NK-mediated cytotoxicity against autologous HLA class I EBV LCL cells did not occur upon mAb-mediated disruption of HLA/KIR interactions. Unlike normal donors, in these patients, only the simultaneous mAb-mediated masking of HLA class I and 2B4 led to reconstitution of cytotoxicity (28). Although not shown, similar results could be obtained by the simultaneous masking of HLA class I and NTB-A. Thus, unlike in normal individuals, in XLP patients, clearance of HLA-deficient EBV-infected cells would be impaired because of the occurrence of inhibitory rather than activating interactions between 2B4, NTB-A, and their ligands. In this context, different studies reported that down regulation of HLA class I molecules occurs during EBV infection (44–46). However, this event may occur "in vivo" only at given stages of EBV infection and/or it may affect one or few HLA class I alleles. Indeed, although most EBV-infected cells may result HLA class I when analyzed with mAbs directed to framework determinants of HLA class I, this analysis is clearly inadequate to reveal a single allelic loss. It should be stressed that down regulation of a single allele renders target cells susceptible to NK cells expressing KIR specific for the missing allele (1). In other reports no inhibitory function of 2B4 has been observed in XLP-NK cells. These studies suggested a "lack of function" of 2B4 (31, 32). Further studies should clarify these divergent results and in particular whether they reflect a heterogeneity of the patients' phenotype or other yet unknown mechanisms. We are presently investigating three additional XLP patients carrying mutations at the SH2D1A locus different from those detected in patients A, B, and C. Preliminary data suggest that also in these patients both 2B4 and NTB-A display inhibitory functions (data not shown). Thus, in six different XLP patients we could obtain consistent results.

These findings may be of particular relevance, as disruption of the interaction between 2B4 or NTB-A with their ligands may lead to restoration of cytolytic function. This may have important implications for therapy of otherwise fatal acute EBV infections in XLP patients. As suggested by the analysis of T cell mediated cytolytic activity in a redirected killing assay, NTB-A fails to trigger cytotoxicity in these cells (data not shown). Also, this finding is reminiscent of previous data on 2B4 molecules (28). Notably, T cells do not express the NKp46 receptor specific for ligand(s) present on murine cells such as the P815 target cell used in redirected killing assays. Thus, CTLs may be unresponsive to mAbs specific for 2B4 and NTB-A in this experimental setting, simply because both molecules act as coreceptors and require for their function a costimulus provided by a true receptor (e.g., NKp46). On the other hand, it is conceivable that, in T cells, other triggering receptors may be physiologically involved in providing the signal required for 2B4- and NTB-A signalling. Along this line, further studies should clarify whether EBV-specific CTLs actually use 2B4 and NTB-A as co-receptors and whether these molecules may inhibit T cell-mediated responses against EBV in XLP patients. Regarding the function of NTB-A in B lymphocytes, studies are in progress in order to clarify this issue. It is of note that so far no SH2D1A could be detected in normal B cells as well as in most B cell lines (41). Thus, it is likely that, in order to transduce signals in B cells, NTB-A may require association with a distinct intracytoplasmic adaptor molecule. In this context, a possible candidate is represented by the recently described EAT-2 molecule that is expressed in B cells and displays high identity with SH2D1A (41). Molecular cloning revealed that NTB-A represents a novel member of the CD2 subfamily (24). Although these molecules display a relatively limited amino acid identity, they are clustered on human chromosome 1 and display a remarkably similar core structure of the Ig-like domains. NTB-A does not contain classical ITAM consensus sequence in the cytoplasmic tail. Different from various activating surface receptors but similar to 2B4 (8–10, 16), NTB-A does not associate with DAP12, CD3, and FcRI signal transducing polypeptides. Moreover, unlike 2B4 (29), NTB-A does not associate with the LAT (not shown). In this context, sequence analysis revealed that NTB-A lacks both the charged amino acid residues in the transmembrane region and the CxC/motif (i.e., a CxC sequence surrounded by positive-charged residues) in the transmembrane/cytoplasmic portion. These motifs have been suggested to play a crucial role in the different receptor/adaptor interactions (4, 47). An additional feature common to 2B4 (28) is the ability of NTB-A to bind SHP-1 and, upon tyrosine phosphorylation, also SH2D1A. Consistent with the latter association, the cytoplasmic tail of NTB-A contains two TxYxxV/I motifs that are thought to represent consensus sequences for the association with SH2D1A (4). Moreover, the amount of SHP-1 associated to NTB-A appears to be reduced upon sodium pervanadate treatment and SH2D1A binding (see FIG. 3). These data are similar to those obtained on 2B4 (28) and suggest that SH2D1A may compete for binding to SHP-1 also in the case of NTB-A. At variance with 2B4, NTB-A is characterized by a classical ITIM motif in the cytoplasmic portion and can associate with SHP-2 upon tyrosine phosphorylation. SHP-2 has been found to associate with both inhibitory and activating receptors (48), suggesting that the final functional outcome of the recruitment of SHP-2 may depend on the functional characteristics of the different SHP-2 specific substrates. Thus, so far, the actual role of this phosphatase in the NTB-A-mediated signalling remains to be determined.

TABLE 1

Surface Expression of MA127-reactive molecules

| Cells | Histotype | MA127 mAb | Anti-2B4 mAb |
|---|---|---|---|
| Resting NK cells | | + | + |
| Activated NK cells | | + | + |
| Resting T cells | | + | + (subset) |
| PHA Blasts | | + | + (subset) |
| Resting B cells | | + | − |
| Thymocytes | | + | + |
| Monocytes | | − | + |
| Granulocytes | | − | − |
| YT | NK cell line | + | + |
| NKL | NK cell line | + | + |
| NK3.2 | NK cell line | + | + |
| NK92 | NK cell line | + | + |
| JA3 | T leukemia | + | + |
| H9 | T leukemia | + | − |
| HSB2 | T leukaemia | + | + |
| Raji | Burkitt lymphona | + | − |
| DAUDI | Burkitt lymphona | + | − |
| LCL 721.221 | EBV-Cell line | + | − |
| U937 | histiocytic lymphona | − | + |
| HL60 | promyelocityc leukemia | − | + |
| TF1 | promyelocityc leukemia | − | + |
| MM6 | promyelocityc leukemia | − | + |
| Eo/A3 | Eosinophilic leukemia | − | + |
| MEL15392 | melanoma | − | − |
| MEL501 | melanoma | − | − |
| F0-1 | melanoma | − | − |
| 1074 mel | melanoma | − | − |

TABLE 1-continued

Surface Expression of MA127-reactive molecules

| Cells | Histotype | MA127 mAb | Anti-2B4 mAb |
|---|---|---|---|
| A549 | lung carcinoma | – | – |
| SMMC | hepatoma | – | – |
| HELA | cervical carcinoma | – | – |
| IGROV-1 | cervical carcinoma | – | – |
| YAC-1 | murine thymoma | – | – |
| BW1502 | murine thymoma | – | – |
| P815 | murine mastocytoma | – | – |
| COS-7 | monkey kidney fibroblast | – | – |

Normal cells and tumor cell lines of different histotype were analysed by immunofluorescence and FACS analysis for reactivity with MA127 and PP35 (anti-2B4) mAbs followed by PE-conjugated goat anti-mouse IgG1. Cells are of human unless otherwise specified.

REFERENCES

1. Moretta, A., C. Bottino, M. Vitale, D. Pende, R. Biassoni, M. C. Mingari, and L. Moretta. 1996. Receptors for HLA-classI molecules in human natural killer cells. *Annu. Rev. Im-munol.* 14:619–648.
2. Lanier, L L. 1998. NK cell receptors. *Annu. Rev. Iminunol.* 16:359–393.
3. Long, E. O. 1999. Regulation of immune responses throughinhibitory receptors. *Annu. Rev. Immunol.* 17:875–904.
4. Moretta, A., C. Bottino, M. Vitale, D. Pende, C. Cantoni, M. C. Mingari, R. Biassoni, and L. Moretta. 2001. Activatingreceptors and co-receptors involved in human natural killercell-mediated cytolysis. *Annu. Rev. Immunol.* 19:197–223.
5. Garrido, F., F. Ruiz-Cabello, T. Cabrera, J. J. Pérez-Villar, M. Lòpez-Botet, M. Duggan-Keen, and P. L. Stern. 1997. Implications for immunosurveillance of altered HLA-class Iphenotypes in human tumours. *Immunol. Today.* 18:89–95.
6. Sivori, S., M. Vitale, L. Morelli, L. Sanseverino, R. Au-gugliaro,C. Bottino, L. Moretta, and A. Moretta. 1997. p 46, a novel natural killer cell-specific surface molecule which mediates cell activation. *J. Exp. Med.* 186:1129–1136.
7. Pessino, A., S. Sivori, C. Bottino, A. Malaspina, L. Morelli, L. Moretta, R. Biassoni, and A. Moretta. 1998. Molecular cloning of NKp46: a novel member of the immunoglobulin superfamily involved in triggering of natural cytotoxicity. *J. Exp. Med.* 188:953–960.
8. Pende, D., S. Parolini, A. Pessino, S. Sivori, R. Augugliaro, L. Morelli, E. Marcenaro, L. Accame, A. Malaspina, R. Bias-soni, et al. 1999. Identification and molecular characteriza-tion of NKp30, a novel triggering receptor involved in natu-ral cytotoxicity mediated by human natural killer cells. *J. Exp. Med.* 190:1505–1516.
9. Vitale, M., C. Bottino, S. Sivori, L. Sanseverino, R. Castri-coni, R. Marcenaro, R. Augugliaro, L. Moretta, and A. Moretta. 1998. NKp44, a novel triggering surface molecule specifically expressed by activated natural killer cells is in-volved in non-MHC restricted tumor cell lysis. *J. Exp. Med.* 187:2065–2072.
10. Cantoni, C., C. Bottino, M. Vitale, A. Pessino, R. Au-gugliaro, A. Malaspina, S. Parolini, L. Moretta, A. Moretta, and R. Biassoni. 1999. NKp44, a triggering receptor involved in tumor cell lysis by activated human natural killer cells, is a novel member of the immunoglobulin superfamily. *J. Exp. Med.* 189:787–796.
11. Moretta, A., R. Biassoni, C. Bottino, M. C. Mingari, and L. Moretta. 2000. Natural cytotoxicity Receptors that trigger human NK-mediated cytolysis. *Immnunol. Today.* 21:228–234.
12. Sivori, S., D. Pende, C. Bottino, E. Marcenaro, A. Pessino, R. Biassoni, L. Moretta, and A. Moretta. 1999. NKp46 is the major triggering receptor involved in the natural cytotoxicity of fresh or cultured human natural killer cells. Correlation between surface density of NKp46 and natural cytotoxicity against autologous, allogeneic or xenogeneic target cells. *Eur.J. Immunol.* 29:1656–1666.
13. Houchins, J. P., T. Yabe, C. McSherry, and F. H. Bach. 1991. DNA sequence analysis of NKG2, a family of related cDNA clones encoding type II integral membrane proteins on hu-man natural killer cells. *J. Exp. Med.* 173:1017–1020.
14. Bauer, S., V. Groh, J. Wu, A. Steinle, J. H. Phillips, L. L. Lanier, and T. Spies. 1999. Activation of NK cells and T cells by NKG2D, a receptor for stress-inducible MICA. *Science.* 285:727–729.
15. Pende, D., C. Cantoni, P. Rivera, M. Vitale, R. Castriconi, S. Marcenaro, M. Nanni, R. Biassoni, C. Bottino, A. Mor-etta, and L. Moretta. 2001. Role of NKG2D in tumor cell lysis mediated by human NK cells: cooperation with natural cytotoxicity receptors and capability of recognizing tumors of non epithelial origin. *Eur. J. Immunol.* 31:1076–1086.
16. Wu, J., Y. Song, A. B. Bakker, S. Bauer, T. Spies, L. L. Lanier, and J. H. Phillips. 1999. An activating immunorecep-tor complex formed by NKG2D and DAP10. *Science.* 285: 730–732.
17. Chang, C., J. Dietrich, A. G. Harpur, J. A. Lindquist, A. Haude, Y. W. Loke, A. King, M. Colonna, J. Trowsdale, and M. J. Wilson. 1999. KAP10, a novel transmembrane adapter protein genetically linked to DAP12 but with unique signal-ing properties. *J. Immunol.* 163:4651–4654.
18. Moretta, A., C. Bottino, G. Tripodi, M. Vitale, D. Pende, L. Morelli, R. Augugliaro, M. Barbaresi, E. Ciccone, R. Millo, and L. Moretta. 1992. Novel surface molecules involved in human NK cell activation and triggering of the lytic machin-ery. *Int. J. Cancer.* 7:6–10.
19. Valiante, N. M., and G. Trinchieri. 1993. Identification of a novel signal transduction surface molecule on human cyto-toxic lymphocytes. *J. Exp. Med.* 178:1397–1406.
20. Gami-Wagner, B. A., A. Purohit, P. A. Mathew, M. Bennett, and V. Kumar. 1993. A novel function-associated molecule related to non-MHC-restricted cytotoxicity mediated by ac-tivated natural killer cells and T cells. *J. Immunol.* 151 :60–70.
21. Kubin, M. Z., D. L. Parsley, W. Din, J. Y. Waugh, T. Davis-Smith, C. A. Smith, B. M. Macduff, R. J. Armitage, W. Chin, L. Cassiano, et al. 1999. Molecular cloning and biological characterization of NK cell activation-inducing ligand, a counterstructure for CD48. *Eur. J. Immunol.* 29:3466–3477.
22. Nakajima, H., M. Cella, H. Langen, A. Friedlein, and M. Colonna. 1999. Activating interactions in human NK cell recognition: the role of 2B4-CD48. *Eur. J. Immunol.* 29: 1676–1683.
23. Sivori, S., S. Parolini, M. Falco, E. Marcenaro, R. Biassoni, C. Bottino, L. Moretta, and A. Moretta. 2000. 2B4 functions as a co-receptor in human natural killer cell activation. *Eur. J. Immunol.* 30:787–793.

24. Tangye, S. G., J. H. Phillips, and L. L. Lanier. 2000. The CD2-subset of the Ig superfamily of cell surface molecule: recep-tor-ligand pairs expressed by NK cells and other immune cells. *Semin. Immunol.* 12:149–157.

25. Boles, K. S., H. Nakajima, M. Colonna, S. S. Chuang, S. E. Stepp, M. Bennett, V. Kumar, and P. A. Mathew. 1999. Mo-lecular characterization of a novel human natural killer cell receptor homologous to mouse 2B4. *Tissue Antigens* 54:27–34.

26. Mathew, P. A., B. A. Garni-Wagner, K. Land, A. Takashima, E. Stoneman, M. Bennett, and V. Kumar. 1993. Cloning and characterization of the 2B4 gene encoding a molecule associ-ated with non-MHC-restricted killing mediated by activated natural killer cells and T cells. *J. Immunol.* 151:5328–5337.

27. Tangye, S., G. S. Lazetic, E. Woollatt, G. R. Sutherland, L. L. Lanier, and J. H. Phillips. 1999. Human 2B4, an activating NK cell receptor, recruits the protein tyrosine phosphatase SHP-2 and the adaptor signaling protein SAP. *J. Immunol.* 162:6981–6985.

28. Parolini, S., C. Bottino, M. Falco, R. Augugliaro, S. Giliani, R. Franceschini, H. D. Ochs, H. Wolf, J. Y. Bonnefoy, R. Biassoni, L. Moretta, L. D. Notarangelo, and A. Moretta. 2000. X-linked lymphoproliferative disease: 2B4 molecules displaying inhibitory rather than activating function are re-sponsible for the inability of NK cells to kill EBV-infected cells. *J. Exp. Med.* 192:337–346.

29. Bottino, C., R. Augugliaro, R. Castricon, M. Nanni, R. Bi-assoni, L. Moretta, and A. Moretta. 2000. Analysis of the molecular mechanism involved in 2B4-mediated NK cell ac-tivation: evidence that human 2B4 is physically and function-ally associated with the linker for activation of T cells (LAT). *Eur. J. Immunol.* 30:3718–3722.

30. Sayos, J., C. Wu, M. Morra, N. Wang, X. Zhang, D. Allen, S. van Schaik, L. Notarangelo, R. Geha, M. G. Roncarolo, et al. 1998. The X-linked lymphoproliferative-disease gene product SAP regulates signals induced through the co-recep-tor SLAM. *Nature.* 395:462–469.

31. Nakajitna, H., M. Cella, A. Bouchon, H. L. Grierson, J. Lewis, C. S. Duckett, J. I. Cohen, and M. Colonna. 2000. Pa-tients with X-linked lymphoproliferative disease have a de-fect in 2B4 receptor-mediated NK cell cytotoxicity. *Eur. J. Immunol.* 30:3309–3318.

32. Tangye, S. G., J. H. Phillips, L. L. Lanier, and K. E. Nichols 2000. Functional requirement for SAP in 2B4-mediated acti-vation of human natural killer cells as revealed by the X-linked lymphoproliferative syndrome. *J. Immunol.* 165:2932–2936.

33. Purtilo, D. T., C. K. Cassel, and J. P. S. Yang. 1974. Fatal in-fectious mononucleosis in familial lymphohistiocytosis. *N. Engl. J. Med.* 201:736.

34. Seemayer, T. A., T. G. Gross, R. M. Egeler, S. J. Pirruccello, J. R. Davis, C. M. Kelly, M. Okano, A. Lanyi, and J. Sumegi. 1995. X-linked lymphoproliferative disease: twenty-five years after the discovery. *Pediatr. Res.* 38:471–478.

35. Nichols, K. E., D. P Harkin, S. Levitz, M. Krainer, K. A. Kolquist, C. Genovese, A. Bernard, M. Ferguson, L. Zuo, E. Snyder, et al. 1998. Inactivating mutations in an SH2 do-main-encoding gene in X-linked lymphoproliferative syn-drome. *Proc. Natl. Acad. Sci. USA.* 95: 13765–13770.

36. Coffey, A. J., R A. Brooksbank, O. Brandau, T. Oohashi, G. R. Howell, J. M. Bye, A. P. Cahn, J. Durham, P. Heath, P. Wray, et al. 1998. Host response to EBV infection in X-linked lymphoproliferative disease results from mutations in an SH2-domain encoding gene. *Nat. Genet.* 20:129–135.

37. Biassoni, R., S. Ferrini, I. Prigione, A. Moretta, and E. O. Long. 1988. CD3-negative lymphokine-activated cytotoxic cells express the CD3 epsilon-gene. *J. Immunol.* 140:1685–1689.

38. Biassoni, R., A. Pessino, C. Bottino, D. Pende, L. Moretta, and A. Moretta. 1999. The murine homologue of the human NKp46, a triggering receptor involved in the induction of natural cytotoxicity. *Eur. J. Immunol.* 29:1014–1020.

39. Cantoni, C., C. Bottino, R. Augugliaro, L. Morelli, E. Mar-cenaro, R, Castriconi, M. Vitale, D. Pende, S. Sivori, R. Milo, et al. 1999. Molecular and functional characterization of IRp60, a member of the immunoglobulin superfamily that. 12 A Novel SH2D1A-associated Triggering Receptor functions as an inhibitory receptor in human natural killer cells. *Eur. J. Immunol.* 29:3148–3159.

40. De la Fuente, M. A., P. Pizcueta, M. Nadal, J. Bosh, and P. Engel. 1997. CD84 leukocyte antigen is a new member of the Ig superfamily. *Blood.* 90:2398–2405.

41. Morra, M., D. Howie, M. Simarro Grande, J. Sayos, N. Wang, C. Wu, P. Engel, and C. Terhorst. 2001. X-linked lymphoproliferative disease: progressive immunodeficiency. *Annu. Rev. Immunol.* 19: 657–682.

42. Mavaddat, N., D. W. Mason, P. D. Atkinson, E. J. Evans, R. J. Gilbert, D. I. Stuart, J. A. Fennelly, A. N. Barclay, S. J. Davis, and M. H. Brown. 2000. Signaling lymphocytic activation molecule (CDw150) is homophilic but self-associates with very low affinity. *J. Biol. Chem.* 275: 28100–28109.

43. Davis, S. J., and P. A. Van der Merwe. 1996. The structure and ligand interactions of CD2: implications for T-cell func-tion. *Immunol. Today.* 17:177–187.

44. Masucci, M. G., S. Torsteindottir, B. J. Colombani, C. Braut-bar, E. Klein, and G. Klein. 1987. Down-regulation of Class I HLA antigens and of the Epstein-Barr virus (EBV)-encoded latent membrane protein (LMP) in Burkitt lymphoma lines. *Proc. Natl. Acad. Sci. USA.* 84:4567–4571.

45. Zeidler, R., G. Eissner, P. Meissner, S. Uebel, R. Tampe, S. Lazis, and W. Hammerschmidt. 1997. Downregulation of TAP1 in B lymphocytes by cellular and Epstein-Barr virus-encoded interleukin-10. *Blood.* 90:2390–2397.

46. Rowe, M., R. Khanna, C. A. Jacob, V. Argaet, A. Kelly, S. Powis, M. Belich, D. Croom-Carter, S. Lee, S. R. Burrows, et al. 1995. Restoration of endogenous antigen processing in Burkitt's lymphoma cells by Epstein-Barr virus latent mem-brane protein-1: coordinate up-regulation of peptide trans-porters and HLA-class I antigen expression. *Eur. J. Immunol.* 25:1374–1384.

47. Bosselut, R., W. Zhang, J. M. Ashe, J. L. Kopacz, L. E. Samel-son, and A. Singer. 1999. Association of the adaptor mole-cule LAT with CD4 and CD8 coreceptors identifies a new coreceptor function in T cell receptor signal transduction. *J. Exp. Med.* 190:1517–1526.

48. Tomasello, E., M. Blery, E. Vely, and E. Vivier. 2000. Sig-naling pathways engaged by NK cell receptors: double con-certo for activating receptors, inhibitory receptors and NK cells. *Semin. Immunol.* 12:139–147.

The invention claimed is:

1. A method of selecting, screening or characterizing a compound for its capacity to modulate a interaction between a NTB-A polypeptide and a binding partner of a NTB-A polypeptide, said method comprising contacting a test compound with a NTB-A polypeptide in the presence of said binding partner selected from SH2D1A and SHP and assessing the capacity of said test compound to modulate the interaction between said NTB-A polypeptide and said binding partner.

2. The method according to claim 1, wherein said binding partner is SH2D1A.

3. The method according to claim 1, wherein said binding partner is SHP.

* * * * *

UNITED STATES PATENT AND TRADEMARK OFFICE
CERTIFICATE OF CORRECTION

PATENT NO.        : 7,138,243 B2
APPLICATION NO.   : 10/484139
DATED             : November 21, 2006
INVENTOR(S)       : Alessandro Moretta, Cristina Bottino and Roberto Biassoni It is certified that error appears in the above-identified patent and that said Letters Patent is hereby corrected as shown below:

Column 1,
Line 60, "InNK cells" should read --In NK cells--.

Column 12,
Line 18, "(Mx367 and MOA110)" should read --(MX367 and MOA110)--.

Column 14,
Line 57, "using RNAzoP" should read --using RNAzo1--.

Column 16,
Line 30, "also to antiNTB-A" should read --also to anti-NTB-A--.

Column 17,
Line 38, "sodium pervanada-tetreated" should read --sodium pervanadate-treated--.

Column 19,
Line 19, "RiNA derived from" should read --RNA derived from--.

Column 23,
Line 28, "*Annu. Rev. Iminunol.*" should read --*Annu. Rev. Immunol.*--.

Column 24,
Line 6, "*Immnunol. Today.*" should read --*Immunol. Today.*--.

Column 25,
Line 41, "Nakajitna, H." should read --Nakajima, H.--.

UNITED STATES PATENT AND TRADEMARK OFFICE
CERTIFICATE OF CORRECTION

PATENT NO. : 7,138,243 B2
APPLICATION NO. : 10/484139
DATED : November 21, 2006
INVENTOR(S) : Alessandro Moretta, Cristina Bottino and Roberto Biassoni It is certified that error appears in the above-identified patent and that said Letters Patent is hereby corrected as shown below:

Column 35,
Line 58, "modulate a interaction" should read --modulate an interaction--.

Signed and Sealed this

Twenty-seventh Day of November, 2007

JON W. DUDAS
*Director of the United States Patent and Trademark Office*